United States Patent
Rossi et al.

(10) Patent No.: US 10,226,173 B2
(45) Date of Patent: Mar. 12, 2019

(54) SYSTEM AND METHOD FOR REAL-TIME MONTAGING FROM LIVE MOVING RETINA

(71) Applicants: Ethan A. Rossi, Pittsburgh, PA (US); Qiang Yang, Rochester, NY (US)

(72) Inventors: Ethan A. Rossi, Pittsburgh, PA (US); Qiang Yang, Rochester, NY (US)

(73) Assignee: University of Rochester, Rochester, NY (US)

( * ) Notice: Subject to any disclaimer, the term of this patent is extended or adjusted under 35 U.S.C. 154(b) by 124 days.

(21) Appl. No.: 15/324,467

(22) PCT Filed: Jul. 6, 2015

(86) PCT No.: PCT/US2015/039214
§ 371 (c)(1),
(2) Date: Jan. 6, 2017

(87) PCT Pub. No.: WO2016/007419
PCT Pub. Date: Jan. 14, 2016

(65) Prior Publication Data
US 2017/0196449 A1 Jul. 13, 2017

Related U.S. Application Data

(60) Provisional application No. 62/021,510, filed on Jul. 7, 2014.

(51) Int. Cl.
*A61B 3/12* (2006.01)
*A61B 3/10* (2006.01)
(Continued)

(52) U.S. Cl.
CPC .......... *A61B 3/1025* (2013.01); *A61B 3/0025* (2013.01); *A61B 3/0058* (2013.01);
(Continued)

(58) Field of Classification Search
CPC ... A61B 3/1025; A61B 3/0025; A61B 3/0058; A61B 3/12; A61B 3/13; A61B 3/14
(Continued)

(56) References Cited

U.S. PATENT DOCUMENTS

2007/0253057 A1* 11/2007 Potsaid ............... G02B 21/002
359/384
2010/0134907 A1* 6/2010 Mann .................. G03F 7/70233
359/858

(Continued)

OTHER PUBLICATIONS

Batten, Christopher F., "Autofocusing and Astigmatism Correction in the Scanning Electron Microscope," 2000, University of Cambridge (89 pages).
(Continued)

*Primary Examiner* — James Greece
(74) *Attorney, Agent, or Firm* — Harris Beach PLLC

(57) ABSTRACT

A scanning LASER ophthalmoscope (SLO) system for real-time montaging includes an adaptive optics scanning light ophthalmoscope (AOSLO) and a wide field scanning light ophthalmoscope (WFSLO). At least one stabilization mirror is controlled by a computer to optically stabilize the AOSLO based at least in part on feedback from the WFSLO. The SLO system also includes a steering means. The SLO system continues to acquire and combine a plurality of AOSLO image frames forming a combined AOSLO image at each of a plurality of narrow field of view (FOV) sites until a predetermined number of images or a predetermined image quality metric (IQM) at each of the combined AOSLO images is achieved. A plurality of the combined AOSLO images is combined to form a SLO montaged image of a wide FOV. A method to montage a plurality of scanning LASER ophthalmoscope (SLO) narrow field of view (FOV) images is also described.

12 Claims, 23 Drawing Sheets

(51) Int. Cl.
*A61B 3/00* (2006.01)
*A61B 3/13* (2006.01)
*A61B 3/14* (2006.01)

(52) U.S. Cl.
CPC .................. *A61B 3/12* (2013.01); *A61B 3/13* (2013.01); *A61B 3/14* (2013.01)

(58) Field of Classification Search
USPC ........................................ 351/205, 206, 246
See application file for complete search history.

(56) References Cited

U.S. PATENT DOCUMENTS

| | | | | |
|---|---|---|---|---|
| 2011/0152845 | A1* | 6/2011 | Hammer | A61F 9/008 606/4 |
| 2014/0104618 | A1* | 4/2014 | Potsaid | G02B 26/105 356/497 |

OTHER PUBLICATIONS

Caviedes, Jorge, et al., "A new sharpness metric based on local kurtosis, edge and energy information," 2004, Signal Processing: Image Communication, vol. 19 (pp. 147-161).
Cheng, Xu, et al., "Predicting subjective judgment of best focus with objective image quality metrics," 2004, Journal of Vision, vol. 4 (pp. 310-321).
Chern, Nathaniel NG Kuang, et al., "Practical Issues in Pixel-Based Autofocusing for Machine Vision," 2001, IEEE International Conference on Robotics and Automation, vol. 3 (pp. 2791-2796).
Cohen, Erez, et al., "No-reference assessment of blur and noise impacts on image quality," 2010, SIVip, (pp. 289-302).
Erasmus, S.J., et al., "An automatic focusing and astigmatism correction system for the SEM and CTEM," 1982, Journal of Microscopy, vol. 127 (pp. 185-199).
Ferzli, R., et al., "No-reference Objective Wavelet Based Noise Immune Image Sharpness Metric," vol. 1 (pp. 405-408).
Firestone, Lawrence, et al., "Comparison of Autofocus Methods for Automated Microscopy," 1991, Cytometry, vol. 12 (pp. 195-206).
Gabarda, Salvador, et al., "Blind image quality assessment through anisotropy," 2007, J. Opt. Soc. Am. A, vol. 24, No. 12 (pp. B42-B51).
Huang, Gang, et al., "Lucky averaging: quality improvement of adaptive optics scanning laser ophthalmoscope images," 2011, Optics Letter, vol. 36 (pp. 3786-3788).
Li, Xin, "Blind Image Quality Assessment," 2002, IEEE International Conference on Image Processing, vol. 1 (pp. I-449-I-452).
Marziliano, Pina, et al., "A No-Reference Perceptual Blur Metric," 2002, International Conference on Image Processing, vol. 3 (pp. III-57-III-60).
Nill, Norman B., et al., "Objective image quality measure derived from digital image power spectra," 1992, Optical Engineering, vol. 31, No. 4 (pp. 813-825).
Saghri, John A., et al., "Image quality measure based on a human visual system model," 1989, Optical Engineering, vol. 28, No. 7 (pp. 813-818).
Shaked, Doron, et al., "Sharpness Measure: Towards Automatic Image Enchancement," 2005, IEEE International Conference on Image Processing, vol. 1 (pp. I-937-I-940).
Stevenson, Scott B., et al., "Correcting for miniature eye movements in high resolution scanning laser ophthalmoscopy," 2005, Ophthalmic Technologies XV, Proceedings of the International Society for Optics and Photonics (SPIE), vol. 5688A (pp. 145-151).
Wang, Shou, et al., "Local Phase Coherence and the Perception of Blur," 2004, Advances in Neural Information Processing Systems, vol. 16 (8 pgs).

\* cited by examiner

WFSLO image

AOSLO image

WFSLO image

AOSLO image steering center (0°, 0°)

steering (+6°, +6°)

FIG. 14B
A sample AOSLO image
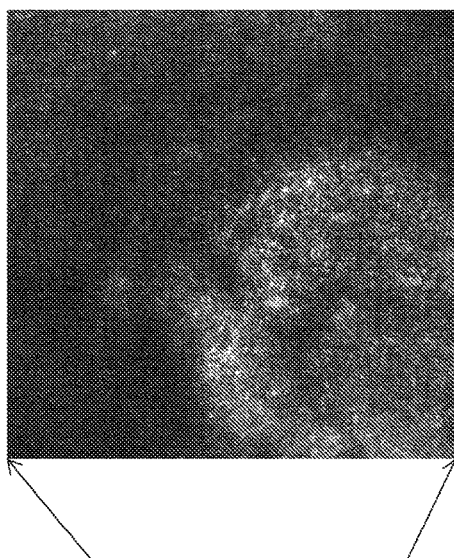
⌐ ─ ┐
│   │  AOSLO image motion on the retina <u>with</u> real-time eye tracking
└ ─ ┘
┌┄┄┄┐
┊   ┊  AOSLO image motion on the retina <u>without</u> real-time eye tracking
└┄┄┄┘
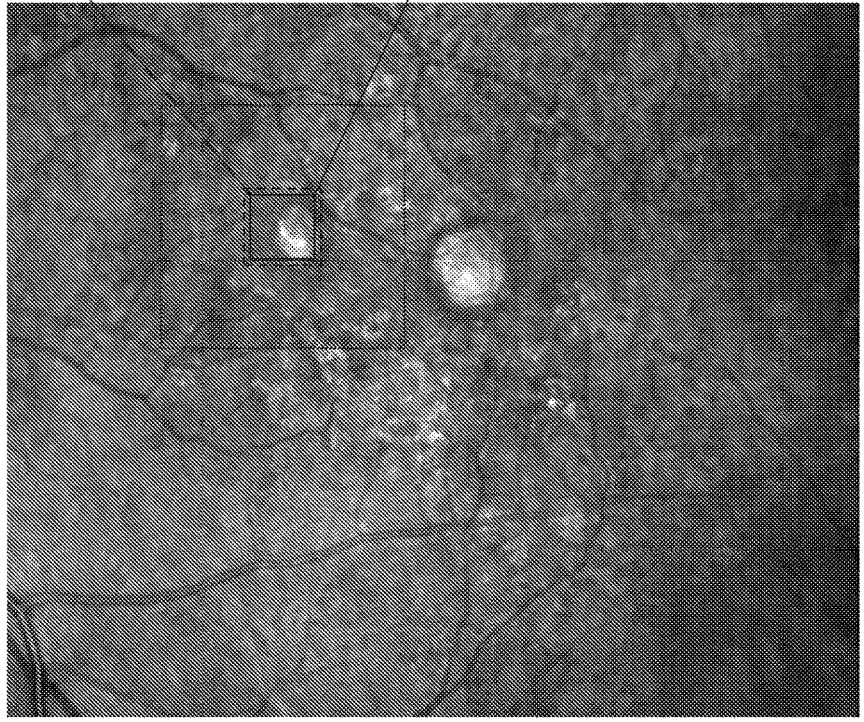
FIG. 14A
A sample WFSLO image from the same retina

SYSTEM AND METHOD FOR REAL-TIME MONTAGING FROM LIVE MOVING RETINA

CROSS-REFERENCE TO RELATED APPLICATIONS

This application is a national stage application under 35 U.S.C. § 371 of PCT Application No. PCT/US2015/039214, filed Jul. 6, 2015, SYSTEM AND METHOD FOR REAL-TIME MONTAGING FROM LIVE MOVING RETINA which claims priority to and the benefit of U.S. provisional patent application Ser. No. 62/021,510, SYSTEM AND METHOD FOR REAL-TIME MONTAGING FROM LIVE MOVING RETINA, filed Jul. 7, 2014, which applications are incorporated herein by reference in their entirety. This application is also related to U.S. provisional patent application Ser. No. 61/879,961, REAL-TIME OPTICAL AND DIGITAL IMAGE STABILIZATION FOR ADAPTIVE OPTICS SCANNING OPHTHALMOSCOPY, filed Sep. 19, 2013, now U.S. Pat. No. 9,226,656, and U.S. provisional patent application Ser. No. 61/929,568, SYSTEM AND METHOD FOR REAL-TIME IMAGE REGISTRATION, filed Jan. 21, 2014, now U.S. Pat. No. 9,406,133, both of which applications and patents are also incorporated herein by reference in their entirety.

STATEMENT REGARDING FEDERALLY FUNDED RESEARCH OR DEVELOPMENT

This invention was made with government support under grants EY014375, EY021786 and EY001319 awarded by the National Institutes of Health. The government has certain rights in the invention.

FIELD OF THE APPLICATION

The invention relates to scanning light ophthalmoscopes (SLO) and particularly to montaging SLO images.

BACKGROUND

An adaptive optics scanning light ophthalmoscope (AOSLO) can provide narrow field of view (FOV) high resolution images of various parts of the human eye such as the retina. Typically many narrow FOV image frames are acquired at a single location. The image frames are then combined by averaging to achieve a high quality averaged narrow FOV image of the single location. The process can be repeated at adjacent areas to create a wider FOV.

In the prior art, the high quality images of several adjacent narrow FOV areas have been combined to form an image of a larger FOV region by manual manipulation of the averaged images using a commercial graphics program such as Photoshop™, available from the Adobe™ Corp. of San Jose, Calif. Such manual processing of narrow field of view (FOV) AOSLO images is time consuming, inefficient, and costly.

SUMMARY

According to one aspect, a scanning LASER ophthalmoscope (SLO) system for real-time montaging includes an adaptive optics scanning light ophthalmoscope (AOSLO) which is communicatively coupled to a computer. A wide field scanning light ophthalmoscope (WFSLO) is also communicatively coupled to the computer. At least one stabilization mirror is controlled by the computer to optically stabilize the AOSLO based at least in part on feedback from the WFSLO. The SLO system also includes a steering means. The SLO system continues to acquire and combine a plurality of AOSLO image frames forming a combined AOSLO image at each of a plurality of narrow field of view (FOV) sites until a predetermined number of images or a predetermined image quality metric (IQM) at each of the combined AOSLO images is achieved. A plurality of the combined AOSLO images is combined to form a SLO montaged image of a wide FOV.

In one embodiment, the SLO system includes a beam splitter, a first optical stabilization mirror, and a second optical stabilization mirror, the first optical stabilization mirror configured to compensate for a large eye motion in a course resolution, and the second optical stabilization mirror configured to compensate for a small residual image motion in a fine resolution.

In another embodiment, the at least one stabilization mirror is controlled by the computer in a closed loop responsive to feedback from both of the WFSLO and the AOSLO.

In yet another embodiment, a fixation target is moved by the computer to increase the FOV beyond a FOV of a SLO system mirror based steering means alone.

In yet another embodiment, at least one mirror of the steering means includes a freeform optical surface.

In yet another embodiment, a control signal of the at least one stabilization mirror is compensated for a nonlinear function of linear motion of at least one stabilization mirror by the computer.

In yet another embodiment, the SLO system further includes a Fundus wide field camera communicatively coupled to the computer.

In yet another embodiment, an AOSLO FOV or an AOSLO pixel density is programmatically controlled by the computer during a calibration of the SLO system by the computer.

According to one aspect, a method to montage a plurality of scanning LASER ophthalmoscope (SLO) narrow field of view (FOV) images including the steps of: providing an optically stabilized SLO having a substantially real-time optical imaging stabilization system and a steering means, the SLO communicatively coupled to a computer; imaging a narrow FOV of a surface of an eye by computer by acquiring one or more image strips of the narrow FOV, followed by: acquiring a successive one or more image strips of at least a part of the narrow FOV; combining by computer the successive one or more image strips of at least a part of the narrow FOV with one or more previously acquired one or more image strips of the at least a part of the narrow FOV to generate a combined image of at least part of the at least a part of the narrow FOV; repeating the step of acquiring a successive one or more image strips of the at least a part of the narrow FOV until a predetermined number of strips is reached; repeating the step of acquiring a successive one or more image strips of at least a part of the narrow FOV to repeating the step of acquiring a successive one or more image strips of the narrow FOV until a predetermined number of strips is reached, until the imaging a narrow FOV of a surface of an eye is complete; and shifting by use of the steering means to another overlapping narrow FOV of the surface of an eye by computer and repeating the step of imaging a narrow FOV of the surface of an eye; repeating the step of shifting to another overlapping narrow FOV of the surface of an eye until a predetermined wide FOV of the surface of an eye has been imaged by a plurality of combined overlapping images; and stitching together by computer either incrementally after each of the narrow FOV is imaged or after the predetermined wide FOV is imaged, each of the plurality of combined overlapping images together to generate a montage wide FOV image of the surface of the eye.

In one embodiment, the one or more image strips include an entire frame.

According yet another aspect, a method to montage a plurality of scanning LASER ophthalmoscope (SLO) narrow field of view (FOV) images including the steps of: providing an optically stabilized SLO having a substantially real-time optical imaging stabilization system and a steering means, the SLO communicatively coupled to a computer; imaging a narrow FOV of a surface of an eye by computer by acquiring one or more image strips of the narrow FOV, followed by: acquiring a successive one or more image strips of at least a part of the narrow FOV; combining by computer the successive one or more image strips of the at least a part of the narrow FOV with one or more previously acquired one or more image strips of the at least a part of the narrow FOV to generate a combined image of the at least a part of the narrow FOV; calculating by computer an image quality metric (IQM) of the combined image using at least a portion of the narrow FOV; comparing by computer the IQM to a pre-determined IQM threshold; repeating the step of acquiring a successive one or more image strips of the narrow FOV until the predetermined IQM threshold is reached; repeating the step of acquiring a successive one or more image strips of at least a part of the narrow FOV to repeating the step of acquiring a successive one or more image strips of the narrow FOV, until the imaging a narrow FOV of a surface of an eye is complete; and shifting by use of the steering means to another overlapping narrow FOV of the surface of an eye by computer and repeating the step of imaging a narrow FOV of the surface of an eye; repeating the step of shifting to another overlapping narrow FOV of the surface of an eye until a predetermined wide FOV of the surface of an eye has been imaged by a plurality of combined overlapping images; and stitching together by computer either incrementally after each of the narrow FOV is imaged or after the predetermined wide FOV is imaged, each of the plurality of combined overlapping images together to generate a montage wide FOV image of the surface of the eye.

In one embodiment, the one or more image strips includes an entire frame.

In another embodiment, the step of providing an optically stabilized SLO includes the step of providing an adaptive optics scanning light ophthalmoscope (AOSLO) having a substantially real-time optical imaging stabilization system.

In yet another embodiment, the step of shifting by the steering means to another overlapping narrow FOV of the surface of an eye includes shifting to another overlapping narrow FOV of the surface of an eye with about a 20% or less overlap.

In yet another embodiment, the step of comparing by computer the IQM includes comparing by computer the IQM based on a power measurement.

In yet another embodiment, the step of comparing by computer the IQM includes comparing by computer the IQM based on a spatial frequency content measurement.

In yet another embodiment, the step of comparing by computer the IQM includes comparing by computer an IQM based on a contrast or sharpness measurement.

In yet another embodiment, the step of comparing by computer the IQM includes comparing by computer the IQM by use of a texture based measurement.

In yet another embodiment, the step of comparing by computer the IQM includes comparing by computer the IQM based on a probability density function measurement.

In yet another embodiment, the method further includes before the step of repeating the step of shifting to another overlapping narrow FOV of the surface of an eye until a predetermined wide FOV of the surface of an eye has been imaged, the step of selecting the pre-determined wide FOV by use of a Fundus wide field camera communicatively coupled to the computer.

The foregoing and other aspects, features, and advantages of the application will become more apparent from the following description and from the claims.

BRIEF DESCRIPTION OF THE DRAWINGS

The features of the application can be better understood with reference to the drawings described below, and the claims. The drawings are not necessarily to scale, emphasis instead generally being placed upon illustrating the principles described herein. In the drawings, like numerals are used to indicate like parts throughout the various views.

FIG. 14A shows an exemplary wide FOV image of the retina of a human eye;

FIG. 14B shows an image of a narrow FOV image of FIG. 14A;

DETAILED DESCRIPTION

Figure 1A:
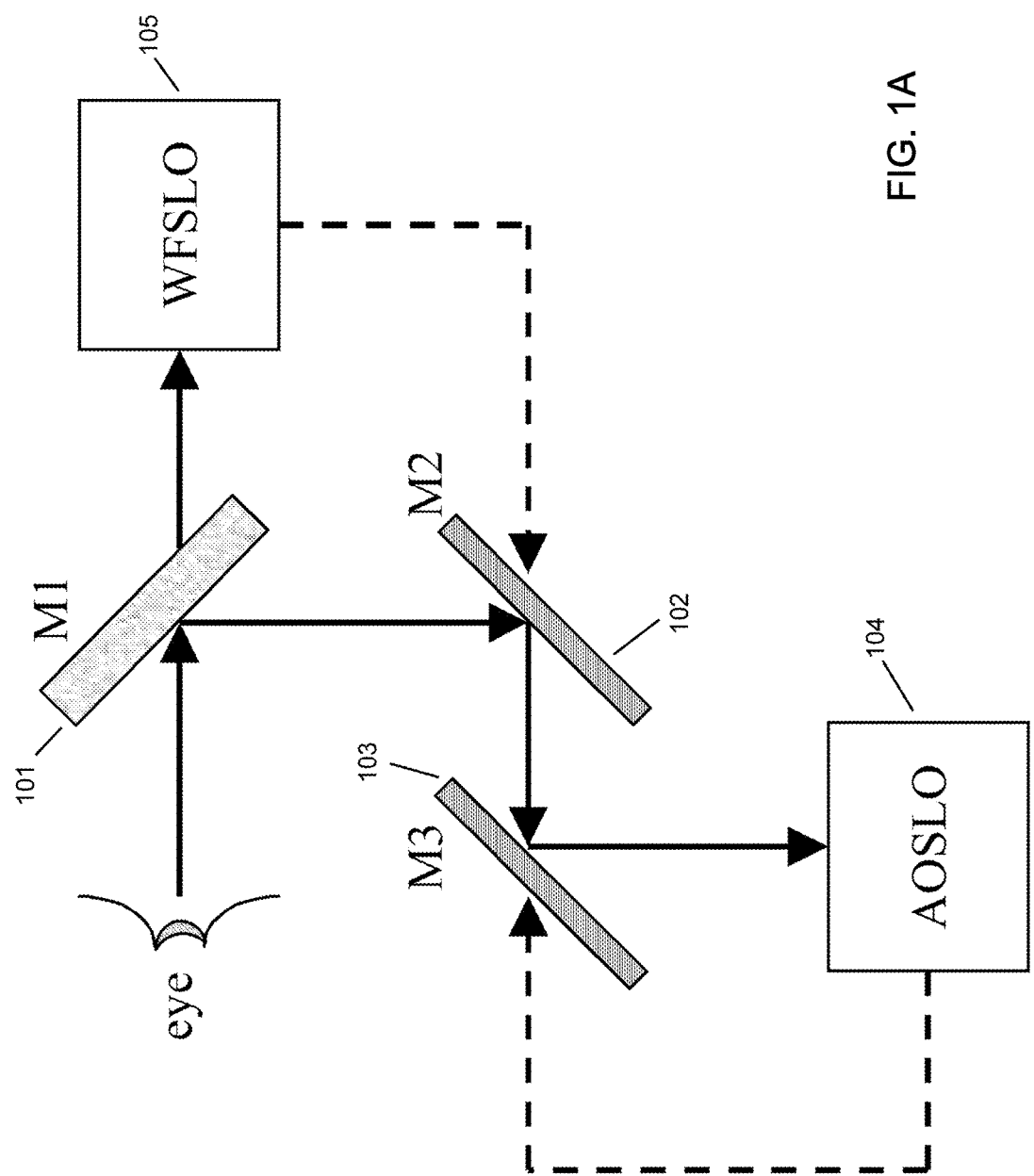
FIG. 1A shows a block diagram of an exemplary real-time eye tracking and optical stabilization system.

In the description, other than the bolded paragraph numbers, non-bolded square brackets ("[ ]") refer to the citations listed hereinbelow.

As described hereinabove, an adaptive optics scanning light ophthalmoscope (AOSLO) can provide narrow field of view (FOV) high resolution images of various parts of the human eye such as the retina. Typically many narrow FOV image frames are acquired at a single location. The image frames are then combined by averaging to achieve a high quality averaged narrow FOV image of the single location. The process can be repeated at adjacent areas to create a wider FOV. One problem is that in the prior art, the high quality images of several adjacent narrow FOV areas have been combined to form an image of a larger FOV region by manual manipulation of the averaged images such as by use of a commercial graphics program such as Photoshop™, available from the Adobe™ Corp. of San Jose, Calif. Such manual processing of narrow field of view (FOV) AOSLO images is time consuming, inefficient, and costly.

Another problem of AOSLO narrow FOV imaging is to limit the number of frames in each narrow FOV image in consideration of minimizing optical LASER power delivered by the AOSLO apparatus to each site of the surface of the eye being imaged. Yet another problem of AOSLO imaging is to limit the time a patient needs to focus on one or more targets to minimize patient discomfort and fatigue.

There is a need for a more efficient way to provide wide FOV images automatically by use of an AOSLO system by computer control and processing.

A new system and method to efficiently and automatically montage (or stitch together) many small FOV high resolution images (e.g., 1.5°×1.5° narrow FOV AOSLO averaged images) to generate a large FOV image (e.g. 10°×10°) by real time computer process offers one solution to problems discussed hereinabove.

The new AOSLO montaging system and method offers several advantages over the prior art. Beyond mere automation, the new approach limits both the number of frames in each image reducing patient optical power dosage both at specific narrow FOV sites as well as total optical exposure over the entire wide field montaged wide FOV. Improvements have been realized in both the time and spatial domains. The description which follows hereinbelow is divided into five parts. Part I introduces AOSLO based montage imaging with improved efficiency both in the time domain and the spatial domain. Part II describes exemplary systems suitable to perform the new method. Part III describes an optical stabilization example having a continuous wide field scanning light ophthalmoscope (WFSLO) based optical stabilization system. Part IV describes an exemplary detailed AOSLO montaging method. Part V uses a series of exemplary optically stabilized AOSLO images and non-stabilized images to further illustrate the efficiency of the new system and method in both the time and spatial domains.

Time Domain Optimization: In the time domain, one or more image quality feedback parameters are monitored substantially in real-time. By comparing the one or more image quality feedback parameters to a pre-determined desired image quality, narrow FOV AOSLO imaging at each narrow FOV site is stopped as soon as the desired image quality for that narrow FOV site is reached.

Image Quality Metrics: Image quality metrics (IQM) use one or more characteristics of an image to describe perceived and/or actual degradation of an image. IQMs can be classified as either full-reference, or no reference. Full-reference IQMs refer to metrics that describe the degradation of a test image with respect to a reference image that is assumed to have perfect quality. No reference IQMs can be used to assess images when no reference exists.

In one exemplary embodiment, a processed image for each narrow FOV AOSLO image is updated substantially in real-time, such as by maintaining an up-to-date averaged image of the previous frames scanned for that site. A signal to noise ratio (SNR) IQM parameter is generated for each now processed image as each new frame is acquired. As soon as the SNR is sufficiently high enough, the particular sited being imaged for the narrow FOV image is complete and AOSLO scanning of that site is stopped. It is understood that the SNR parameter can be based on the entire narrow FOV image or one or more portions of the narrow FOV image.

Other IQM parameters can be alternatively used instead of, or in addition to an image S/N IQM parameter. For example, one or more of the following categories of IQMs described hereinbelow are contemplated to be suitable for use in the new real-time montaging SLO systems and methods described herein as IQM parameters.

Power measure IQMs include, for example, signal-to-noise ratio (SNR) and variance based IQM [10].

Spatial frequency content IQMs include, for example: spatial frequency content of image (MTF, power spectrum, etc.), Shaked-Tast1 metric (high pass/band pass ratio) [8], frequency threshold based IQM [7], autocorrelation/derivative based IQM [11], and modified image spectrum [17].

Contrast and sharpness (e.g. edge contrast) IQMs include, for example, contrast-to-noise ratio (CNR, entropy, acutance, sharpness IQMs (such as the one used in equation (1) in ref [2]), acutance, noise immune sharpness IQM (in wavelet domain) [9], and no-reference IQM based on edge sharpness, random noise and structural noise levels [15].

Texture based IQMs include, for example, entropy, anisotropy based IQMs [16], and gray level co-occurrence matrix (GLCM) [2].

Histogram (probability density function) based IQMs include, for example, histogram threshold [7], histogram entropy [13], and kurtosis [12].

Spatial domain optimization: Another way to limit the time of a montage AOSLO image acquisition is to reduce the overlap of the narrow FOV image sites. In the prior art, it was common to use about a 50% overlap of AOSLO narrow FOV imaging sites. In the new system and method, it was realized that overlap can be significantly reduced to as little as a 5% overlap. One reason that less overlap is needed is because the feedback system in the time domain provides more accurate narrow FOV images which are easier to stitch together using any suitable image stitching techniques. Such image stitching techniques are well known in the art. However, stitching performance (accuracy and speed) is a function of the quality of the individual images, thus the improvement described herein includes providing better quality narrow FOV images more efficiently in less time with less overlap. Another reason is that the steering system combined with optical stabilization allows for precise targeting of the image acquisition area in the spatial domain. By contrast, prior art systems and methods relied primarily on patient fixation for targeting, which was imprecise, necessitating large amounts of overlap.

PART II—Exemplary Systems Suitable to Perform the New Method

One exemplary system stabilizes image motion of an AOSLO in real time by dynamically updating the positions of one or more stabilization mirrors to compensate for eye motion. One exemplary implementation of a suitable real-time eye tracking and optical stabilization system is shown in FIG. 1A. Technical details of a similar implementation have been described in U.S. Provisional Patent Application Ser. No. 61/880,057, REAL-TIME OPTICAL AND DIGITAL IMAGE STABILIZATION FOR ADAPTIVE OPTICS SCANNING OPHTHALMOSCOPY, filed Sep. 19, 2013 (hereinafter, "the '057 application") and U.S. Provisional Patent Application Ser. No. 61/886,507, REAL-TIME OPTICAL AND DIGITAL IMAGE STABILIZATION FOR ADAPTIVE OPTICS SCANNING LASER OPHTHALMOSCOPY, filed Oct. 3, 2013 (hereinafter, "the '507 application"). Both of the '057 and '507 applications are incorporated herein by reference in their entirety for all purposes.

Figure 1B:
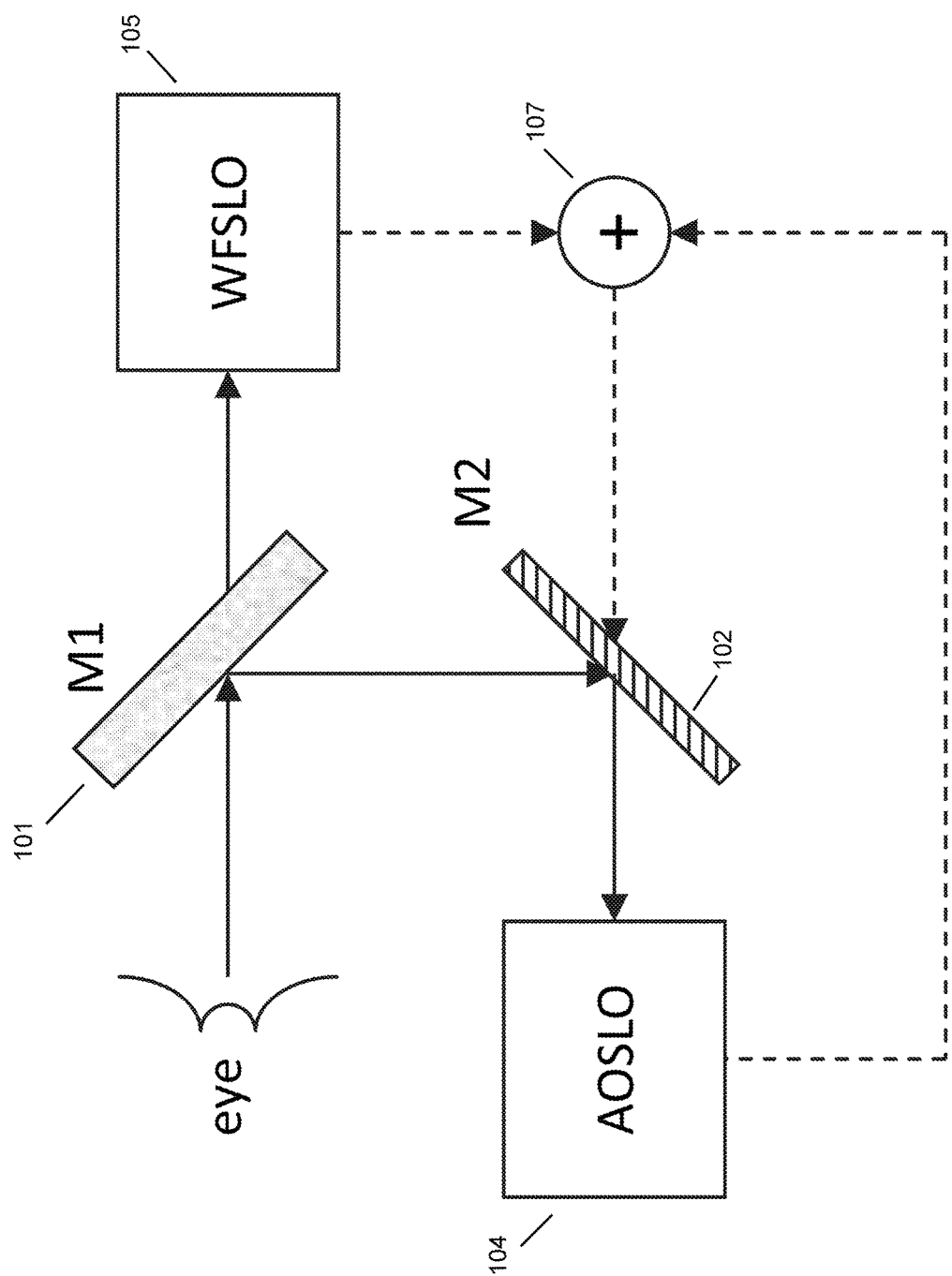
FIG. 1B shows block diagram of another exemplary real-time eye tracking and optical stabilization system where a single stabilization mirror is employed to perform open-loop control with WFSLO and closed-loop control with AOSLO.

An exemplary motion tracking process suitable for use with an AOSLO apparatus, such as the AOSLO apparatus of FIG. 1A and FIG. 1B, has also been described in detail in U.S. Pat. No. 9,226,656, REAL-TIME OPTICAL AND DIGITAL IMAGE STABILIZATION FOR ADAPTIVE OPTICS SCANNING OPHTHALMOSCOPY, filed Sep. 19, 2013 (hereinafter, "the '656 patent"). An exemplary data flow control process has been described in detail in U.S. Pat. No. 9,406,133, SYSTEM AND METHOD FOR REAL-TIME IMAGE REGISTRATION, filed Jan. 21, 2014 (hereinafter, "the '568 application '133 patent"). Both of the '656 and '133 patents are also incorporated herein by reference in their entirety for all purposes.

The exemplary optical system of FIG. 1A includes both a large FOV and small FOV imaging system. In FIG. 1A, M1 101 is a beam splitter; M2 102 and M3 103 are stabilization minors. Solid arrows show optical paths and dashed arrows show electronic and software paths for controlling the minors. The exemplary wide field of view scanning laser ophthalmoscope (WFSLO) 105 has a maximum FOV of about 27°×22.5° and AOSLO 104 has a maximum of about 2.7°×2.7° FOV (about a 1.5°×1.5° FOV is also commonly used). Each of the FOVs can be made smaller and are programmable under computer control.

Control of stabilization mirrors, such as, for example, M2 102 of the WFSLO 105 has been described in have also been described in U.S. Provisional Patent Application Ser. No. 61/913,177, AOSLO AND WF-SLO FOR STEERABLE, STABILIZED, HIGH RESOLUTION RETINAL IMAGING AND REAL-TIME OPTICAL STABILIZATION AND DIGITAL REGISTRATION, filed Dec. 6, 2013, now U.S. patent application Ser. No. 14/490,449, by Canon, U.S.A. INC., (hereinafter, "the '449 application") and U.S. Provisional Patent Application Ser. No. 61/930,794, REAL-TIME OPTICAL STABILIZATION AND DIGITAL IMAGE REGISTRATION IN ADAPTIVE OPTICS SCANNING LIGHT OPHTHALMOSCOPY, filed Dec. 6, 2013 also, now U.S. patent application Ser. No. 14/490,449, by Canon, U.S.A. INC. (hereinafter, "the '449 application"). The '449 application is incorporated herein by reference in its entirety for all purposes. Other co-pending applications disclosed herein (and incorporated by reference herein) also include descriptions of steering means suitable for use in a system and method for real-time montaging from live moving retina. Additional robust and smooth control such as, for example, of M2 102 from WFSLO 105 has also been described in U.S. Provisional Patent Application Ser. No. 61/934,201, SYSTEMS AND METHODS FOR SIMULTANEOUS MEASUREMENT OF TEAR FILM LIPID AND AQUEOUS LAYERS THICKNESSES USING OPTICAL COHERENCE TOMOGRAPHY AND STATISTICAL ESTIMATORS, filed Jan. 31, 2014, now U.S. patent application Ser. No. 14/548,067, (hereinafter, "the '067 Application"). The '067 application is incorporated herein by reference in its entirety for all purposes.

In the exemplary embodiment of FIG. 1A, M2 102 is controlled in the open loop of WFSLO 105 which does not 'see' the action of M2 102, but M3 103 works in the closed loop of AOSLO 104 which does 'see' residual image motion because of the action of M3 103. M2 102 compensates for large amplitude eye motion in coarse resolution and M3 103 compensates small amplitude residual eye motion in fine resolution.

FIG. 1B shows block diagram of another exemplary real-time eye tracking and optical stabilization system where a single stabilization mirror M2 102 is employed to perform open-loop control with WFSLO 105 and closed-loop control with AOSLO 104. If the eye motion is defined as $(X_{eye,t}, Y_{eye,t}, \theta_{eye,t})$ at time t, and the action of M2 102 with motion contribution from the WFSLO 105 output is $$(X_{wf,t}, Y_{wf,t}, \theta_{wf,t}), \quad (1)$$

then the residual image motion that can be 'seen' from the AOSLO is $$(\delta X_t, \delta Y_t, \delta \theta_t) = (X_{eye,t}, Y_{eye,t}, \theta_{eye,t}) - (X_{wf,t}, Y_{wf,t}, \theta_{wf,t}) \quad (2)$$

without taking account into mechanical latency from M2 102. AOSLO detects the residual motion $(\delta X_t, \delta Y_t, \delta \theta_t)$, and feeds it back to M2 102 in the closed loop form, $$(X_{ao,t-1}, Y_{ao,t-1}) + g_{ao}(\Delta X_{ao,t}, \Delta Y_{ao,t}) \quad (3)$$

where $(X_{ao,t-1}, Y_{ao,t-1})$ is the accumulated M2 102 motion from AOSLO, $(\Delta X_{ao,t}, \Delta Y_{ao,t})$ is the measurement of eye motion from AOSLO at time t, and $g_{ao}$ is closed-loop gain of AOSLO. The signal combiner at 107 adds Equation (1) and Equation (3) to output the result $$\Theta_{wf}(X_{wf,t}, Y_{wf,t}, \theta_{wf,t}) + \Theta_{ao}[(X_{ao,t-1}, Y_{ao,t-1}) + g_{ao}(\Delta X_{ao,t}, \Delta Y_{ao,t})] \quad (4)$$

to M2 102. $\Theta_{wf}$ and $\Theta_{ao}$ are rotation operators of WFSLO and AOSLO respectively. In FIG. 1A, $(X_{wf,t}, Y_{wf,t}, \theta_{wf,t})$ is applied on M2 102 and $(X_{ao,t-1}, Y_{ao,t-1}) + g_{ao}(\Delta X_{ao,t}, \Delta Y_{ao,t})$ is applied on M3 103, but in FIG. 1B they are added together by the signal combiner 107 and applied on the single M2 102.

Figure 2:
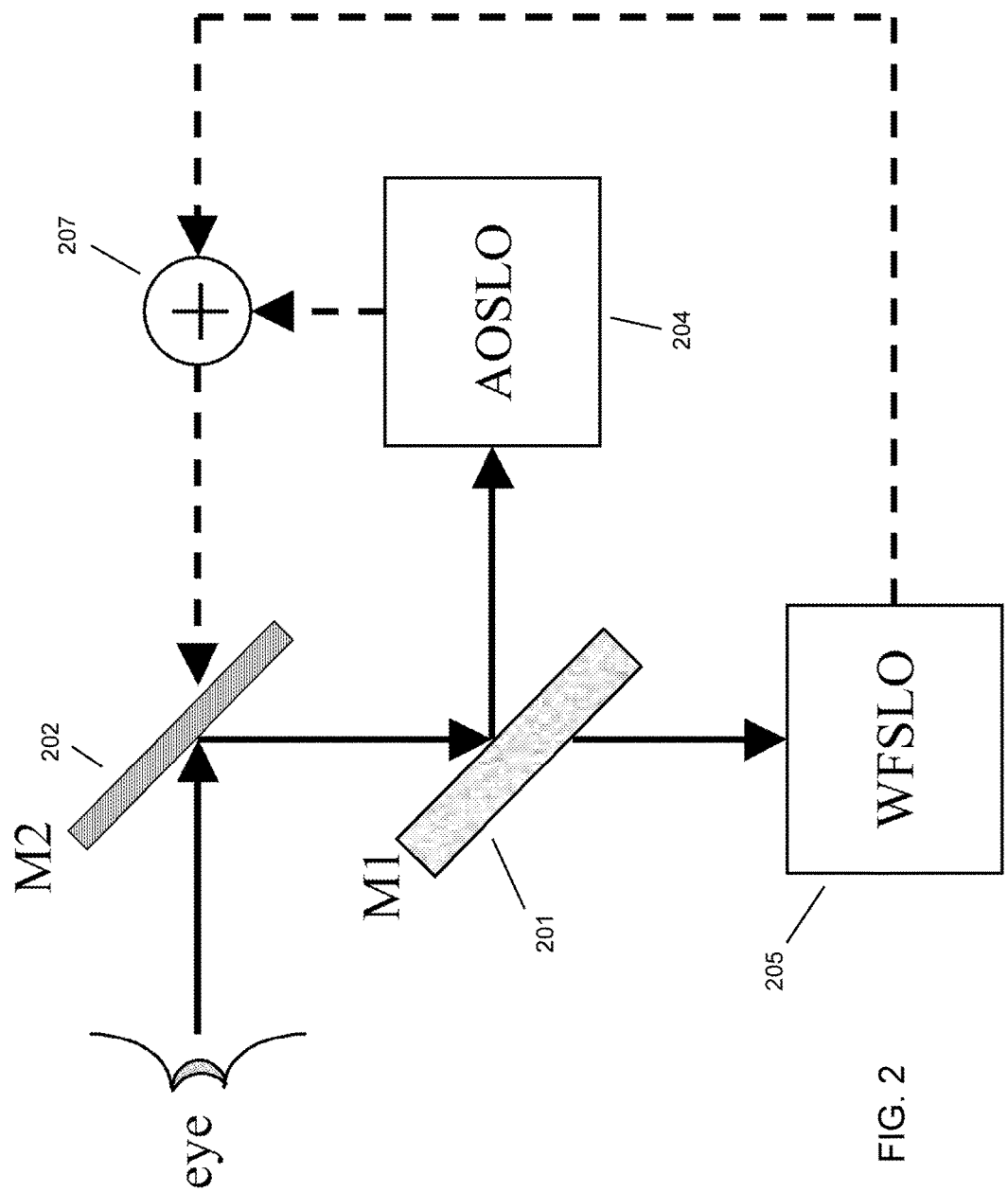
FIG. 2 shows a block diagram of another exemplary real-time eye tracking with complete closed-loop control from both WFSLO and AOSLO.

In another exemplary embodiment, a simplified optical implementation with eye tracking can be implemented in FIG. 2. In the exemplary system of FIG. 2, both WFSLO 205 and AOSLO 204 are implemented in the closed loop of M2 202 which becomes the only stabilization mirror in the eye tracking system. In the exemplary implementation of FIG. 2, light from the eye is first relayed to the stabilization mirror M2 202, and it is then split to WFSLO 205 and AOSLO 204 by M1 201. This approach allows both WFSLO 205 and AOSLO 204 to 'see' the action of M2, therefore, both WFSLO 205 and AOSLO 204 detect residual image motion where the majority of image motion caused by eye motion has been compensated by the action of M2 202. The signal combiner 207 adds measurements of eye motion from AOSLO and WFSLO. WFSLO calculates residual image motion at time t (e.g., $\Delta X_{wf,t}$, $\Delta Y_{wf,t}$, $\Delta \theta_{wf,t}$) from the WFSLO images, and AOSLO calculates residual image motion at time t (e.g., $\Delta X_{ao,t}$, $\Delta Y_{ao,t}$) from the AOSLO images. The computer operates the signal combiner 207 to synthesize these two sets of data by appropriate gains to update M2, e.g., in the formula, $(X_{t+1}, Y_{t+1}) = (X_t, Y_t) + g_{wf}\Theta_{wf}(\Delta X_{wf,t}, \Delta Y_{wf,t}, \Delta \theta_{wf,t}) + g_{ao}\Theta_{ao}(\Delta X_{ao,t}, \Delta Y_{ao,t})$ where $(X_t, Y_t)$ is existing position of M2 202 at time t, $(X_{t+1}, Y_{t+1})$ is new position of M2 202 to be updated at time t+1, $g_{wf}$ and $g_{ao}$ are closed-loop gains of WFSLO 205 and AOSLO 204 respectively, and $\Theta_{wf}$ and $\Theta_{ao}$ are rotation operators of WFSLO and AOSLO respectively.

The data flow processes described in the '133 patent are also suitable for use with the system of FIG. 2.

In SLO systems using a signal combiner to combine (typically by adding) output data from both of the WFSLO system and the AOSLO system it is understood that such output data could be analog or digital in any combination thereof. Moreover, it is understood that there can be modification or calibration of either or both of the WFSLO system and the AOSLO system output data before the combination function. Typically, such modification or calibration can include, but is not limited to, gain and/or offset calibration.

Figure 3A:
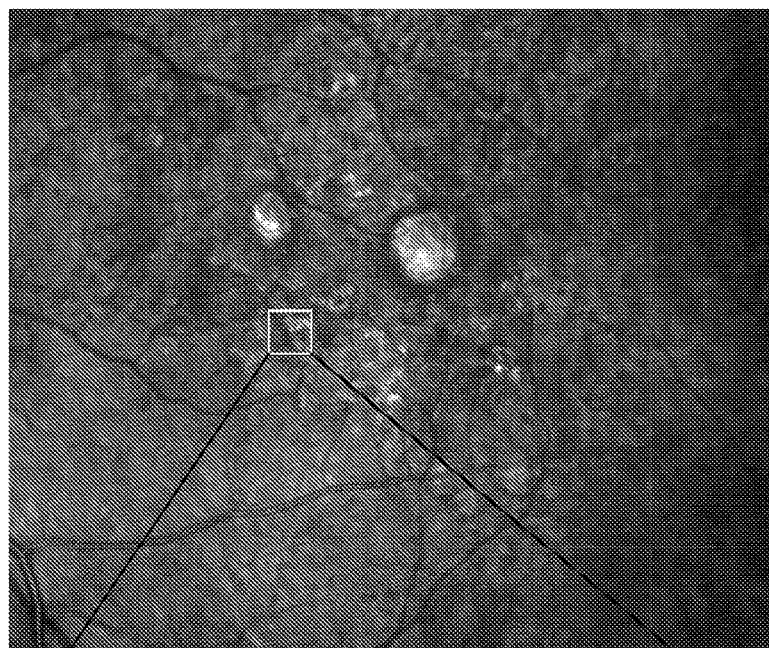
FIG. 3A shows an exemplary image WFSLO image.
Figure 3B:
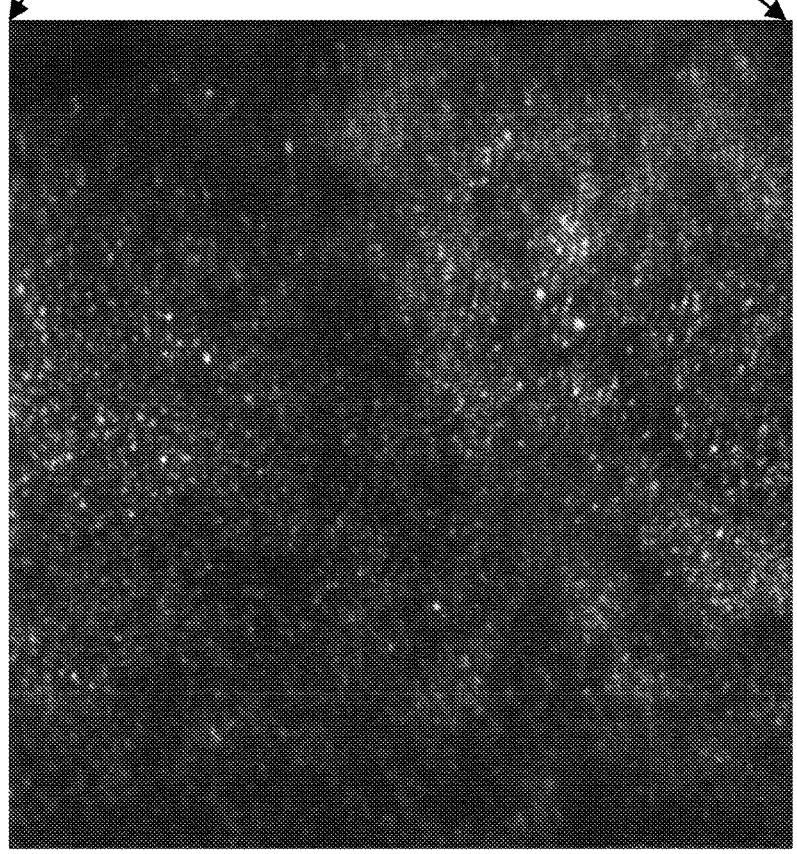
FIG. 3B shows an exemplary image AOSLO image of FIG. 3A.

FIG. 3A (WFSLO image) and FIG. 3B (AOSLO image) show two typical images from WFSLO and AOSLO which were obtained from the two optical systems. A single frame from the imaging system contains substantially more noise than the averaged image. Each image (FIG. 3A, FIG. 3B) is an average of multiple registered frames. Averaging of registered images is one exemplary method that can be used to achieve a high signal-to-noise ratio (SNR) image.

An exemplary suitable optical system, such as the AOSLO systems of FIG. 1A, FIG. 1B and FIG. 2, typically have the capability to quickly steer (e.g., in 1-2 seconds) a small AOSLO imaging field (e.g., about a 1.5°×1.5° narrow FOV) to any location across a wide range of retinal positions, e.g., about a 15°×15° relatively wide FOV in current implementations. This quick steer feature can be achieved, for example, by implementing a 2-dimensional steering mirror or two 1-dimensional steering mirrors to physically steer the imaging area of the AOSLO. Exemplary suitable SLO steering systems and methods are described in the co-pending '057 provisional patent application as referenced hereinabove.

Steering means: SLO system steering means including WFSLO and AOSLO steering techniques as used by the SLO systems and methods of montaging as described herein, including, for example, quick steering, can be performed by any suitable motion of a reflective or partially reflective surface, typically a mirror. There can be a dedicated steering mirror (not shown in FIG. 1A, FIG. 1B, or FIG. 2). Or, any controllable mirror of either of the WFSLO and the AOSLO systems can be controlled in a dual function mode, where the mirror performs both the relatively large angle steering function, as well as a fine or course image stabilization function. Either or both of the WFSLO system or the AOSLO system are understood to include either a steering surface (typically a steering mirror or a combined function with a stabilization minor). There could also be a separate SLO system controllable steering surface (typically a minor). In the methods described in more detail hereinbelow, as in steps such as, for example, shifting to another overlapping narrow FOV of said surface of an eye by computer and repeating said step of imaging a narrow FOV of said surface of an eye, the function of shifting to another overlapping narrow FOV is understood to be accomplished primarily by a steering surface, possibly augmented by a shift of a fixation target for exceptionally large areas beyond those directly accessibly by the steering minor.

Suitable steering means functions and mirrors have also been described in the '449 application. Other co-pending applications disclosed herein (and incorporated by reference herein) also include descriptions of steering means suitable for use in a system and method for real-time montaging from live moving retina.

In some embodiments, at least one of the minors of the steering means can be a freeform surface configured to compensate for distortions introduced when steering to large angles. In some embodiments, there is a small "steering mirror" that directs the light onto a large spherical mirror. This configuration allows for targeting different retinal locations (e.g. steering to different narrow FOVs). However, because the large mirror is spherical, it introduces distortions in the AO field at the more extreme angles. It is contemplated that a steering mirror having a freeform surface could minimize these distortions.

Figure 4A:
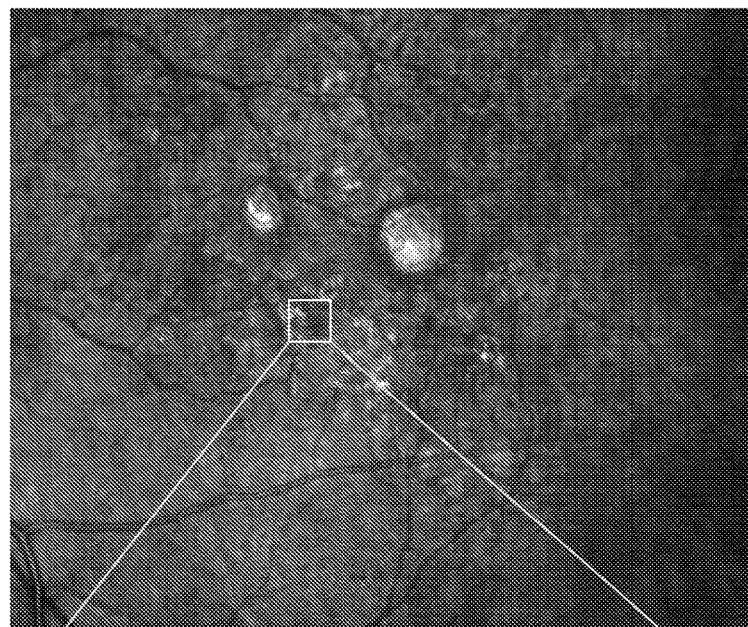
FIG. 4A shows another exemplary WFSLO image.
Figure 4B:
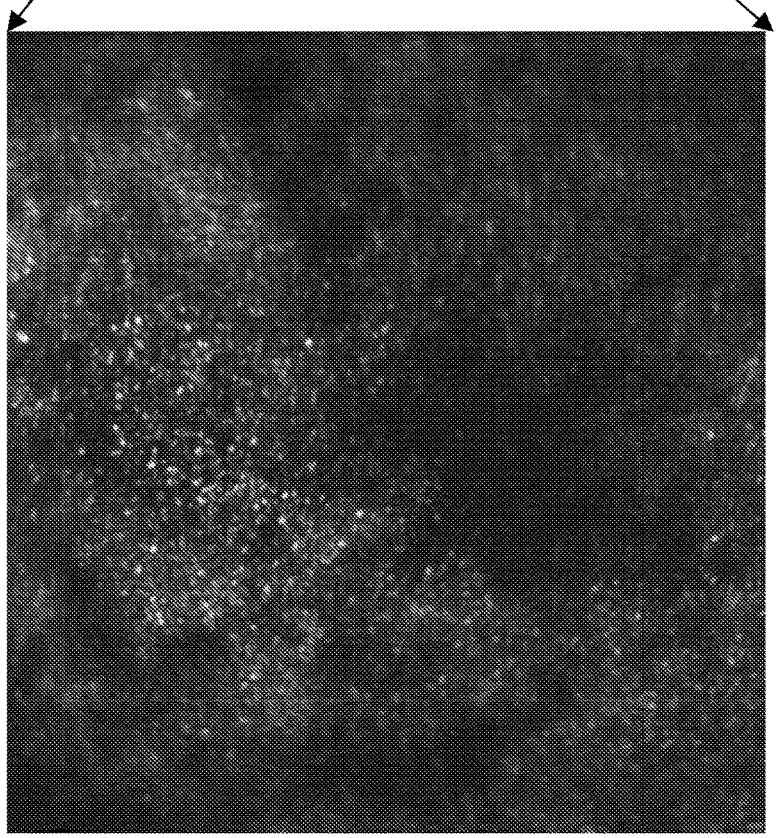
FIG. 4B shows an exemplary AOSLO image of FIG. 4A.

As illustrated in FIG. 4A (WFSLO image) and FIG. 4B (AOSLO image), an AOSLO can quickly be steered to the next retinal location by changing control signals sent to the steering minor. In the past, such "steering" was accomplished by adjusting the location of a fixation target and asking the subject to point their eyes at (look at and refocus on) a fixation target. With the new feature of AOSLO apparatus steering, the subject needs to look at only one location as long as the target AOSLO imaging area is inside the relatively wide FOV steering range, e.g., about 15°×15° in a current exemplary implementation.

Figure 5:
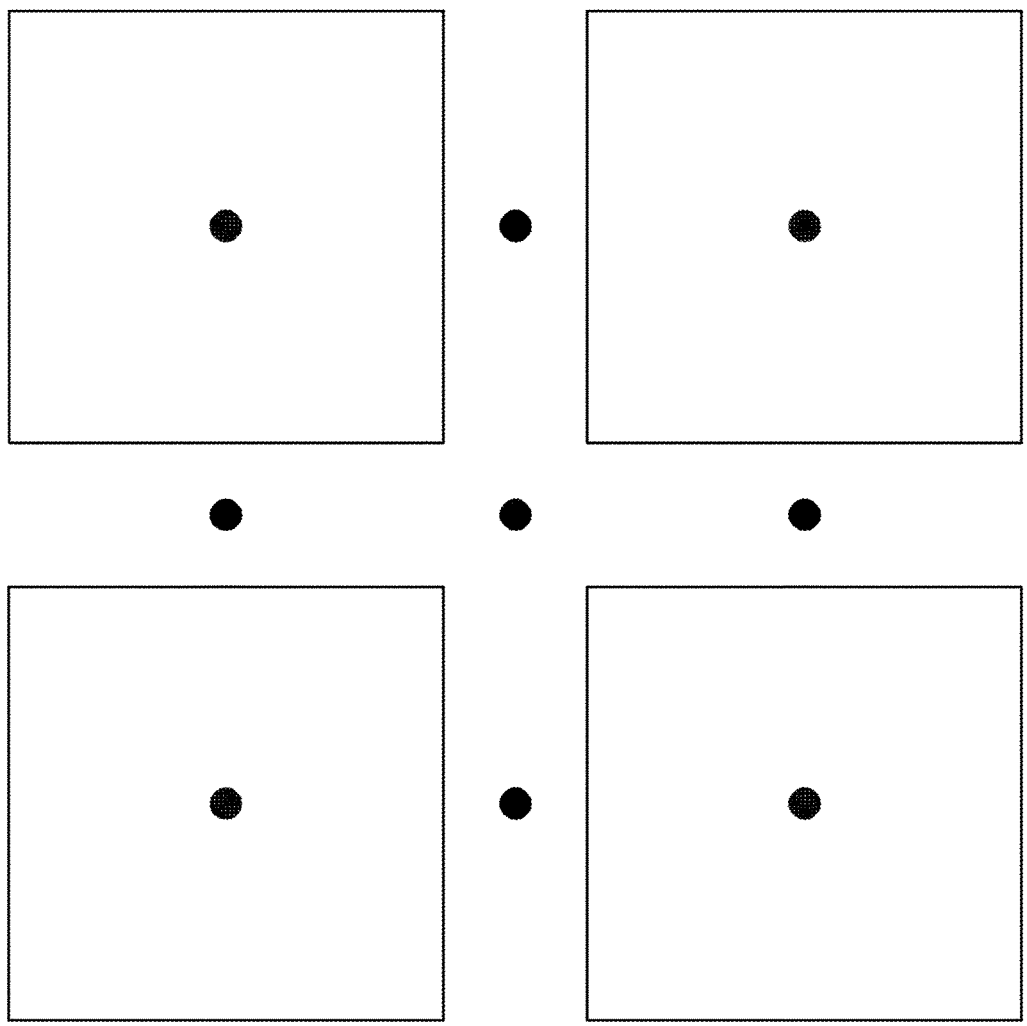
FIG. 5 is a drawing illustrating ±7.5° image boxes with fixation targets.

In some cases, even the relatively large about 15°×15° steering range is insufficient to cover a desired region of interest (ROI). For example, where there are one or multiple lesions in a diseased eye, it can be desirable to cover a still larger ROI. In such cases where even a 15°×15° steering range is insufficient, the new optical system provides a programmable fixation target which can be set at any location in ±10° of the fovea (the central area of the retina where an image of a carefully fixated target falls in a normal eye). For example, in FIG. 5, steering about ±7.5° (shaded areas) around each fixation target (solid dots) allows the system to access a still larger about 35°×35° FOV of the retina.

Real-time stabilization from both WFSLO and AOSLO and real-time steering of the AOSLO imaging field make efficient real-time montaging possible. A method of real-time montaging for obtaining a large field of view montage from many small field of view AOSLO images is now described in more detail hereinbelow.

Figure 6:
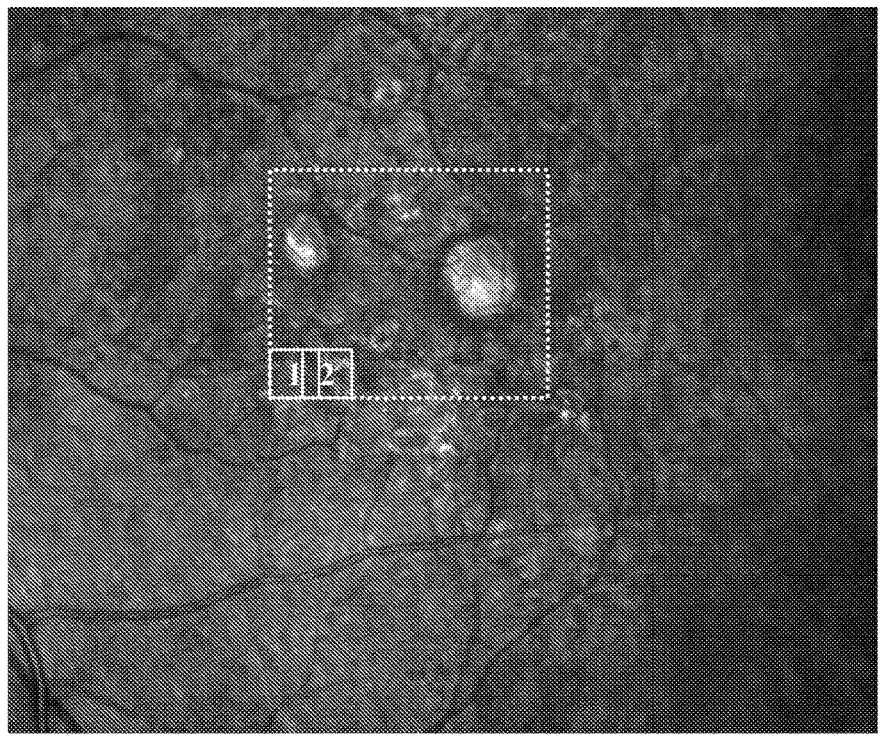
FIG. 6 shows an exemplary image illustrating montaging of a ROI from an eye with age-related macular degeneration (AMD)

FIG. 6 shows an example of montaging an ROI from an eye with age-related macular degeneration (AMD). In FIG. 6, the ROI is the area enclosed within the dotted rectangular area. Overlapping AOSLO images 1 and 2 are understood to be the first two images of a series of averaged images 1, 2, ... n (areas beyond 2, not shown in FIG. 6) which cover the entire dotted ROI show in FIG. 6. Multiple high resolution high SNR AOSLO images, as shown in the amplified parts in FIG. 3A and FIG. 3B and FIG. 4A and FIG. 4B, are montaged (i.e. stitched together) to seamlessly cover about an about 8°×7° ROI in FIG. 6. It was realized that several technical issues as described in more detail hereinbelow should be considered to implement efficient and seamless real-time montaging.

There should be a sufficient yet minimal AOSLO image overlap when the AOSLO imaging area is steered from one location to the next. As illustrated in FIG. 6, when AOSLO imaging area is steered from location 1 to location 2, a minimum amount of overlap is used to give the montaging process algorithm enough information to stitch the two AOSLO images together. The overlapped area should be as small as possible to sweep through the whole ROI in the least amount of time and/or the least amount of AOSLO imaging areas.

Fixational eye motion causes image motion in the live videos obtained in both the AOSLO and WFSLO. Because of the smaller FOV and higher resolution, the same magnitude of eye motion causes more image motion in the AOSLO than in the WFSLO. Particularly in diseased eyes with poor fixation, the AOSLO image field can move across several degrees. This makes targeting specific areas in the AOSLO with steering extremely difficult without optical stabilization because it does not guarantee that a desired AOSLO imaging area (location 2), e.g. by steering 1° toward right, will be obtained. The use of real-time optical stabilization as has been implemented in our prototype systems has substantially minimized the issues caused by eye motion. Our recent experiments in 10 normal eyes and 7 diseased eyes showed that the residual RMS error after WFSLO optical stabilization is ~21 μm from diseased eyes and ~10 μm from normal eyes. The peak-to-peak AOSLO image motion after WFSLO optical stabilization is ~1/10 of the typical AOSLO FOV size in diseased eyes and ~1/20 of the typical AOSLO FOV size in normal eyes.

Figure 7:
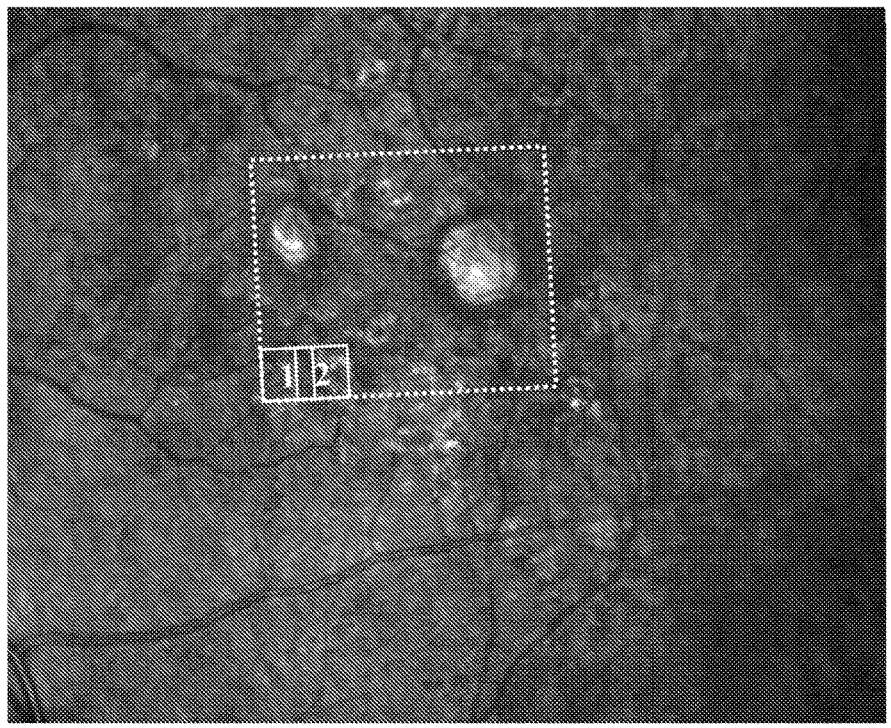
FIG. 7 shows an exemplary image illustrating image rotation caused by eye and/or head rotation.

Eye motion and/or head motion can also cause torsion (rotation about the line of sight) in both AOSLO and WFSLO images, as illustrated, for example, by the WFSLO image of FIG. 7. A real-time montaging process algorithm should detect the torsion, steer the AOSLO imaging area to the correct retinal location, and digitally (or optically, if possible) correct the torsion from the AOSLO images. Detection of torsion is implemented using the WFSLO in our current system.

AOSLO FOV can be distorted nonlinearly by the optical system at different steering locations in our current implementation. It is contemplated that in future optical designs, such as by use of freeform optical surfaces, such distortions could be minimized Freeform optical surfaces are optical surfaces with complex shapes that are not rotationally symmetric. In our implemented systems, at the steering center, the AOSLO scans an about 1.5°×1.5° square, but at the four steering corners (~±7.5°, ~±7.5°), the AOSLO actually scans a slightly rotated and stretched diamond.

AOSLO imaging location is typically a nonlinear function of linear motion of the steering mirror. The nonlinearity can be a result of both the optical system and of the biometry of each individual eye (such as the axial length and curvature of the retina). For example, at different retinal locations, a 1° steering command from the steering mirror can steer the actual AOSLO imaging area about <1°, ~1°, or >1° and across a straight or curved path across the retina.

Determining a ROI: 1) An ROI can be defined by a different imaging system. For example, a patient could go to the clinic where a doctor takes a photograph of the eye with a fundus camera and marks the ROI on that image. The doctor then sends the patient and image to a facility having an system and method as described herein and the image from the doctor could then be used to define the ROI for imaging by cross-correlating it with the WF-SLO image of our new system. See, for example, exemplary step 13300 hereinbelow.

2) In other embodiments, instead of having a WFSLO in our new imaging system as described herein, we use a fundus camera instead. In such an embodiment, the fundus camera provides us with a wide field of view image instead of the wide field of view image coming from a WFSLO. In this case, the ROI is defined using that image as in point because in this embodiment there may be no WFSLO present in the system.

After realizing all of these technical issues, a prototype system and method for real-time montaging was implemented using the approaches/procedures described in more detail hereinbelow.

PART III—Optical Stabilization Example: Continuous Optical Stabilization from WFSLO One exemplary new method for continuous optical stabilization from WFSLO includes the steps of:

Step A: Start WFSLO optical stabilization, and keep stabilization on until the whole AOSLO montage is finished or the fixation target moves to a different location.

Step B: To make WFSLO optical stabilization as stable as possible based on our image-based process algorithm where a reference image is chosen from a video sequence and the subsequent images are registered to this reference image, the process algorithm calculates eye motion from three parameters (x, y, θ) where (x, y) is translation, and θ is torsion.

Figure 8:
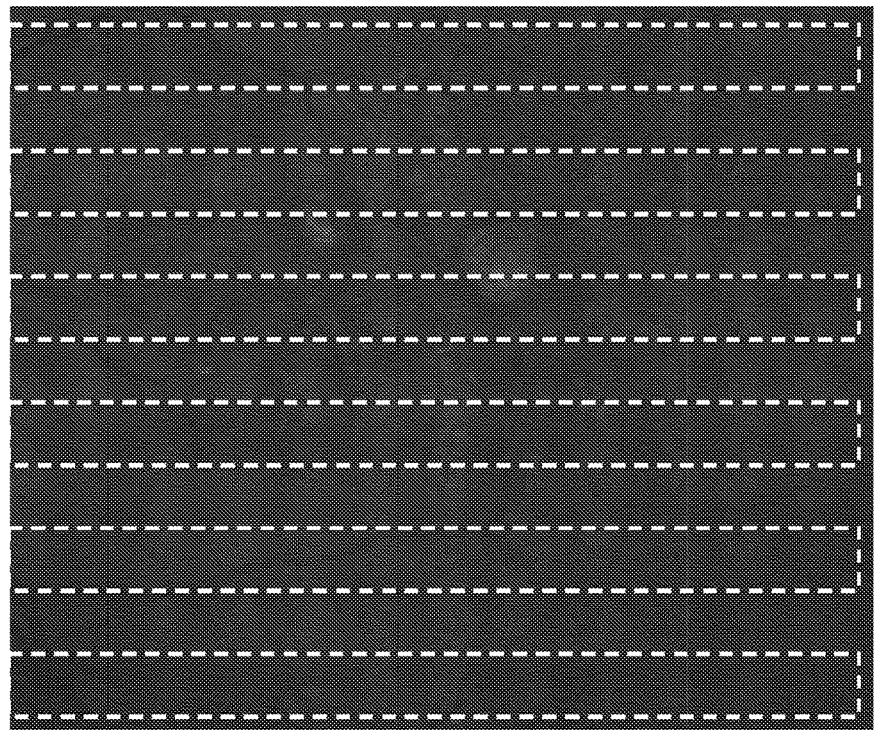
FIG. 8 shows an exemplary image illustrating a method to calculate fine eye motion by use of a frame image divided into multiple strips.

Step C: To calculate fine eye motion to drive the stabilization mirror (M2 and/or M3) more smoothly, each frame of an image is further divided into multiple strips to obtain motions from individual strips, as illustrated in FIG. 8. Suitable process algorithms as are described in the '656 patent referred to hereinabove can be used.

Figure 9:
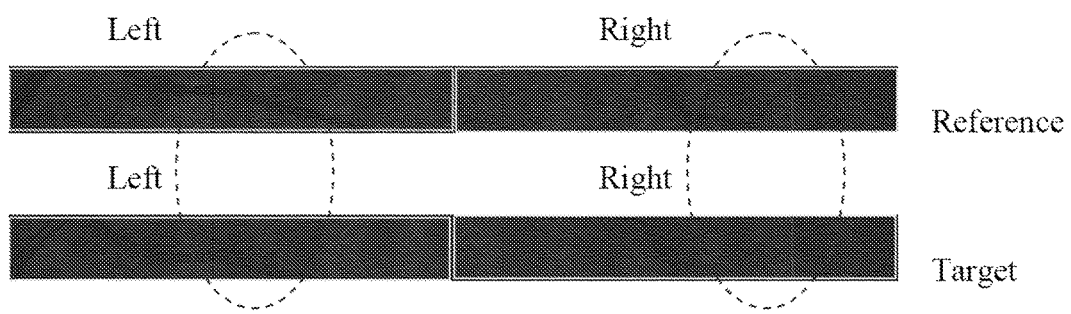
FIG. 9 shows an exemplary image illustrating calculation of translation and torsion based on an image-based cross correlation.

Step D: In the exemplary image frame of FIG. 9, the top strip is from the reference frame, and the bottom strip is from the target frame. To calculate translation and torsion at the same time, each long strip is further divided into two sub strips, a left one and a right one, as shown in FIG. 9. The process algorithm calculates two pairs of motion from the left strips and the right strips independently. If the left two sub strips give motion $(x_L, y_L)$ and the right two sub strips give motion $(x_R, y_R)$, then the eye motion will be approximately, $$x=(x_L+x_R)/2, \qquad (1)$$

$$y=(y_L+y_R)/2, \qquad (2)$$

$$\theta=(y_L+y_R)\times 2/W, \qquad (3)$$

where W is the width of the image. One suitable approach was described by Stevenson[1], et. al. in "Correcting for miniature eye movements in high resolution scanning laser ophthalmoscopy" in Ophthalmic Technologies XV, Proceedings of The International Society for Optics and Photonics (SPIE), Vol. 5688A, 2005. A similar exemplary implementation was also described in the '067 application.

Step E: Due to the limitation from the approach in FIG. 9, the process algorithm can fail when the torsion magnitude θ is larger than a certain amount. Under this situation, the process algorithm automatically updates the reference frame to a new reference frame which occurs right before the calculations of Equations (1)-(3). The motion of this frame is recorded as $(x_{i,f}, y_{i,f}, \theta_{i,f})$, and the subscript (i,f) denotes the ith reference frame during the whole stabilization sequence.

Step F: If the case of i=0 is for the first reference frame, $(x_{0,f}, y_{0,f}, \theta_{0,f})$ will be (0, 0, 0) as this is the case of autocorrelation of the first reference frame. The subsequent reference frames and their motions are represented in the form $F_i$ and $(x_{i,f}, y_{i,f}, \theta_{i,f})$ where $(X_{i,f}, y_{i,f}, \theta_{i,f})$ is the motion of reference frame $F_i$ relative to its previous reference frame $F_{i-1}$. As a consequence, motion of the reference frame $F_i$ relative to the first reference frame $F_0$ will be, $$X_{i,f} = \sum_{j=1}^{i} x_{j,f} \tag{4}$$

$$Y_{i,f} = \sum_{j=1}^{i} y_{j,f} \tag{5}$$

$$\Theta_{i,f} = \sum_{j=1}^{i} \theta_{j,f} \tag{6}$$

Step G: From Equations (1)-(6), the net motion of each single strip in FIG. 8 is, $$X = X_{i,f} + x \tag{7}$$

$$Y = Y_{i,f} + y \tag{8}$$

$$\Theta = Y_{i,f} + \theta \tag{9}$$

Step H: The stabilization mirror M2 is able to compensate translation only, hence (X, Y) is sent to M2 to optically compensate eye motion.

Step I: Torsion Θ is digitally recorded in WFSLO.

Step K: Torsion Θ is concurrently sent from WFSLO to AOSLO to dynamically update steering data, and to digitally rotate AOSLO images.

Part IV—Process Example

One exemplary embodiment of optical stabilization, digital registration, image averaging, and image montaging by AOSLO is shown in the flowchart which extends over the five drawing pages of FIGS. 13A, 13B, 13C, 13D, and 13E.

Step 13100 After WFSLO has stabilized AOSLO images such as after the process detects torsion and steers the AOSLO imaging area to the correct retinal location, the WFSLO sends the current reference frame to AOSLO.

Figure 10:
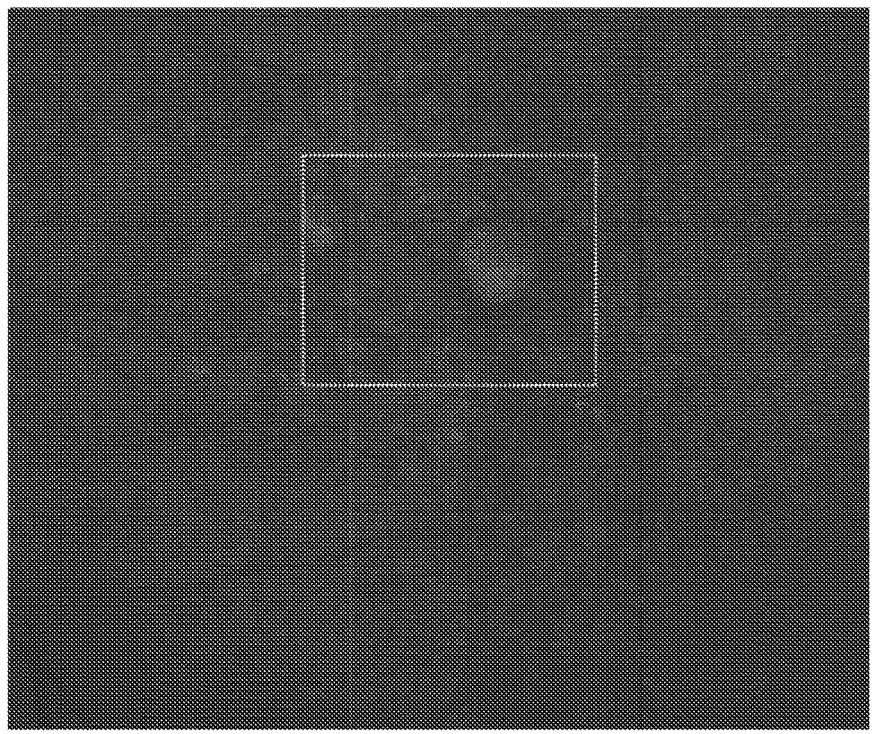
FIG. 10 shows an exemplary WFSLO image that allows a user to define a ROI.

Step 13200 This WFSLO reference frame allows users to define the ROI, as illustrated by the dotted rectangle in FIG. 10 which allows users to define a ROI. In this exemplary implementation, we use a single frame, however in other embodiments, an averaged image (e.g. FIG. 3A, FIG. 3B, FIG. 4A, FIG. 4B, FIG. 5, FIG. 6) will be implemented. In this ROI, data from multiple AOSLO imaging areas will be recorded and processed. A high SNR image from each imaging area is obtained and montaged in real time.

Step 13300 Operators use a pointing method, such as, for example, the mouse click (could also be, for example, a touch screen or any other suitable user interaction means) to define this area on the WFSLO image, or the desired coordinates of this area are entered into the software manually by use of a software process graphical user interface (GUI). Optionally, an image obtained from another wide field of view imaging system, such as an image of a fundus camera can be used to define the ROI. In cases where the ROI is defined by use of a second imaging system, e.g. a fundus camera, the wide field image from the other imaging system is scaled and cross-correlated with the WFSLO image to determine the precise location of the ROI on the WFSLO image.

Figure 11:
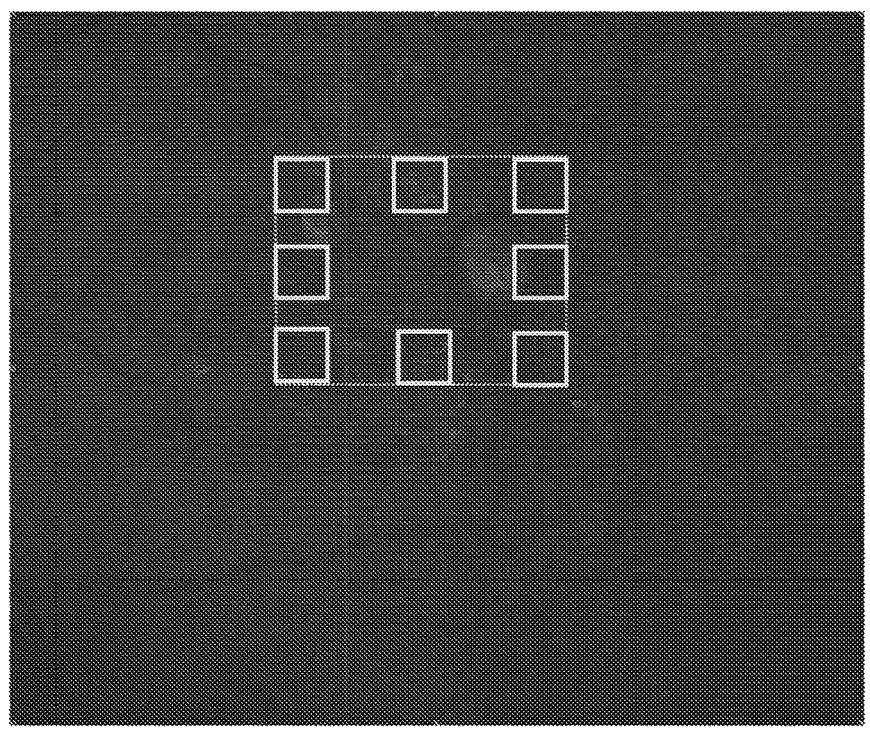
FIG. 11 shows an exemplary image illustrating a calibration method related to optical distortion.

Step 13400 Due to optical distortions, such as where the AOSLO FOV is distorted nonlinearly by the optical system at different steering locations or where the AOSLO imaging location is a nonlinear function of linear motion of a steering mirror, a calibration phase may be used. In some embodiments, the system does a quick calibration, such as, for example, is illustrated in FIG. 11. One method is to quickly steer the AOSLO imaging area to the squares of FIG. 11 one by one (one square at a time). A cross correlation or other image based approaches can then be executed to match each of the AOSLO areas to the WFSLO image, to determine distortion of AOSLO imaging area and to calibrate the nonlinearity of steering.

Step 13500 In step 13400, the AOSLO FOV and/or pixel density can further be variable and programmable to facilitate calibration.

Step 13600 Once steps 13400 and 13500 are finished, real-time montaging is executed.

Step 13700 Real-time montaging can run completely automatically or semi-automatically.

Step 13800 In an exemplary complete automatic mode, the following procedure is executed.

Step 13801 The steering mirror moves AOSLO image area to the first location, for example, box "1" of FIG. 6.

Step 13802 Once the steering is complete, AOSLO software automatically determines a reference frame by choosing one A) from an eye-drift session with the slowest eye motion and B) this frame has mean pixel value and standard deviation higher than user defined threshold value or a user defined IQM threshold, and then starts optical stabilization (controlling M3) and digital registration.

Step 13803 An auto-focus thread is activated to determine the focus to obtain the best AOSLO image of the desired retinal layer of interest. Auto-focusing information comes from AOSLO images and is based on contrast detection and/or other image quality metrics. This process algorithm is able to auto focus at different layers across the thickness of the retina.

Step 13804 AO focus is adjusted by updating the deformable mirror, or other optical and electronic components using methods such as those described in U.S. provisional patent application Ser. No. 61/875,808, APPARATUS AND METHOD FOR AUTOMATIC POSITION CONTROL IN AN OPTICAL SYSTEM AND APPLICATIONS, filed Sep. 10, 2013, now U.S. patent application Ser. No. 14/482,195 (hereinafter, "the '195 application"). The '195 application is incorporated herein by reference in its entirety for all purposes.

Step 13805 Once the best focus has been found, the AOSLO software optionally updates the current reference frame, and starts image recording and image averaging. When a certain amount of images/strips are accumulated to have a high SNR image, an averaged image and the stabilized video is saved to the hard drive. The number of images/strips to be acquired at each location may be fixed or can vary based on a calculation of image SNR or another IQM, with the latter being more efficient as only as many frames as necessary to obtain the desired SNR or IQM at each location is obtained.

Optionally, AOSLO software obtains images from multiple different layers of the retina by changing focus.

Optionally, AOSLO software obtains images from multiple different imaging channels simultaneously. These could include channels for fluorescence or dark field imaging methods (such as split-detector, or offset aperture) that have could have weak signals. These channels would be co-registered simultaneously and stitched together in real-time using the information from the reflectance channel. When acquiring images from multiple different imaging channels simultaneously, the number of frames registered and averaged for each channel may differ. The SNR or other IQM used to determine the number of strips or frames to acquire may operate on the channel with the weakest signal, or each channel may have its own fixed number of frames or operate on its own SNR or other IQM. For example, typically weaker signals will use more data averaging to produce a good image. Also, each channel could use a different fixed number of frames or use a different IQM to optimize data acquisition for the image being obtained.

Figure 12A:
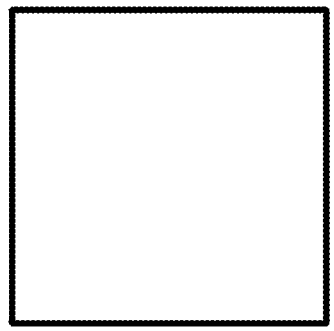
FIG. 12A shows a drawing illustrating the shape of an AOSLO imaging area at steering center (0°, 0°)
Figure 12B:
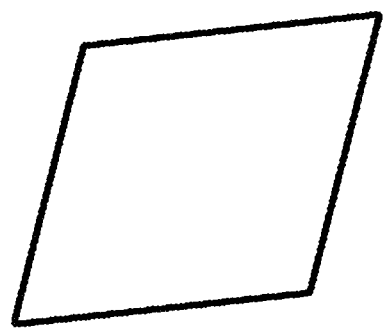
FIG. 12B shows a drawing illustrating the shape of an AOSLO imaging area at steering (+6°, +6°)
Figure 13A:
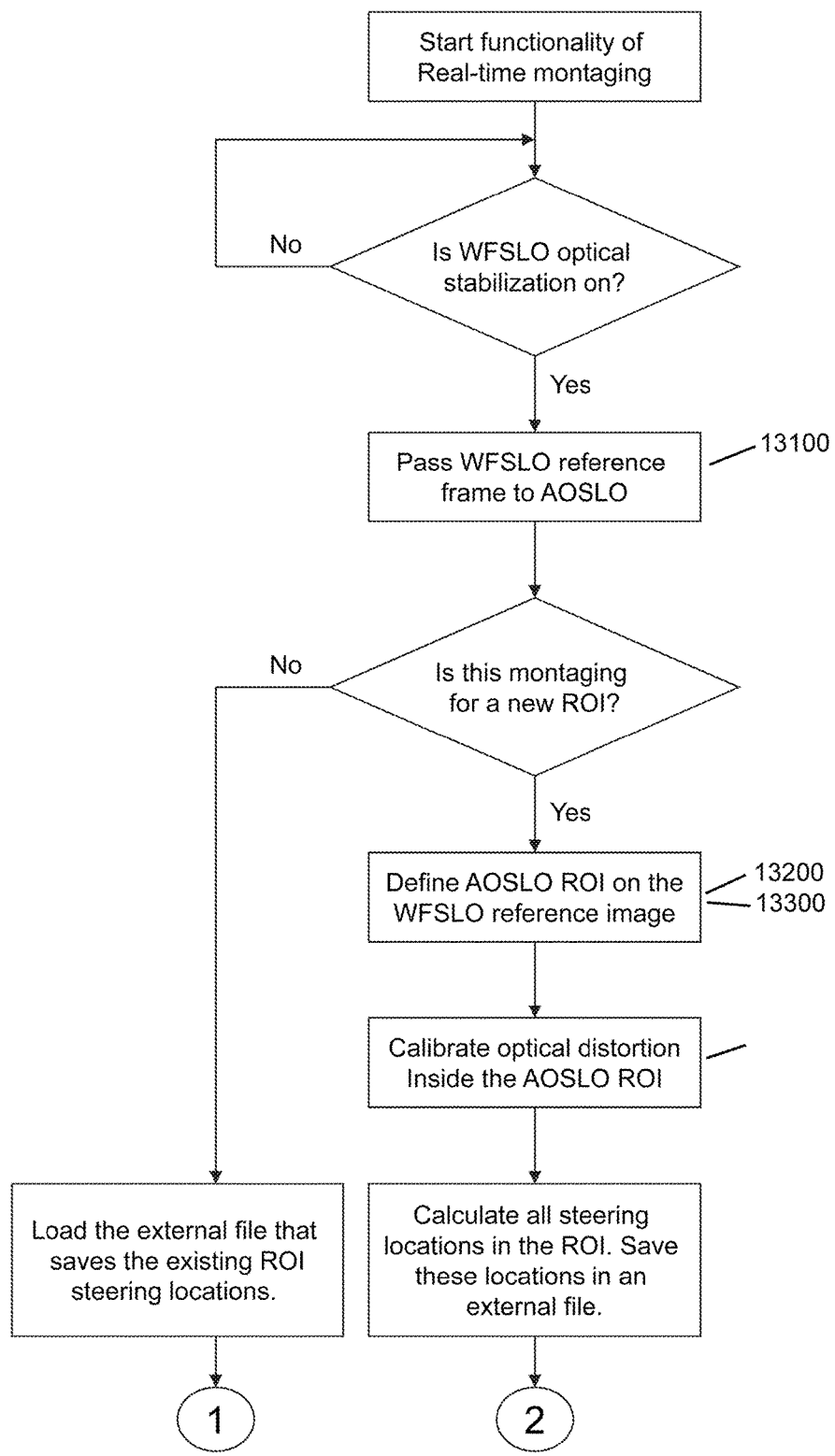
FIG. 13A shows a first page of an exemplary flow chart of a method of AOSLO montaging.
Figure 13B:
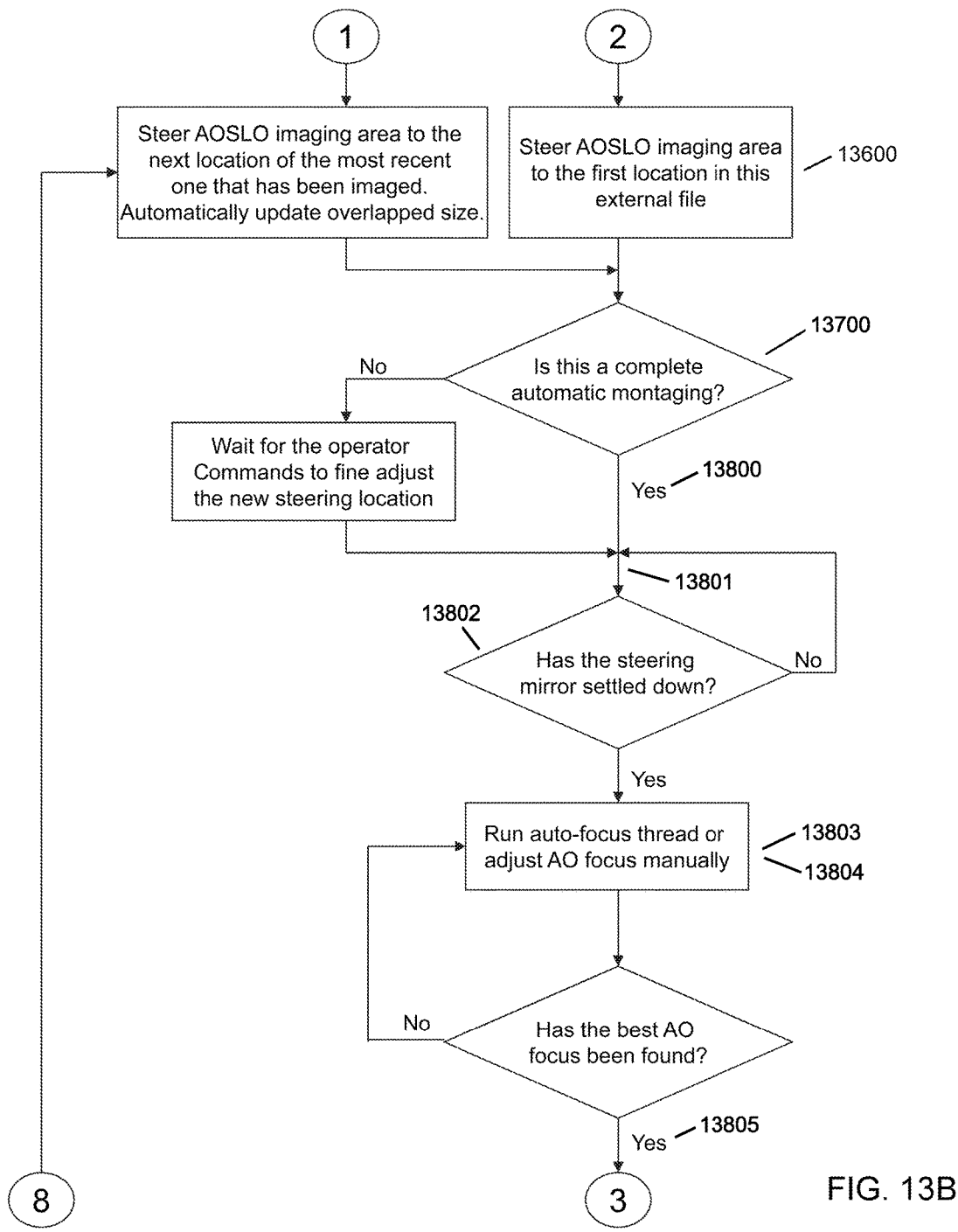
FIG. 13B shows a second page of the exemplary flow chart.
Figure 13C:
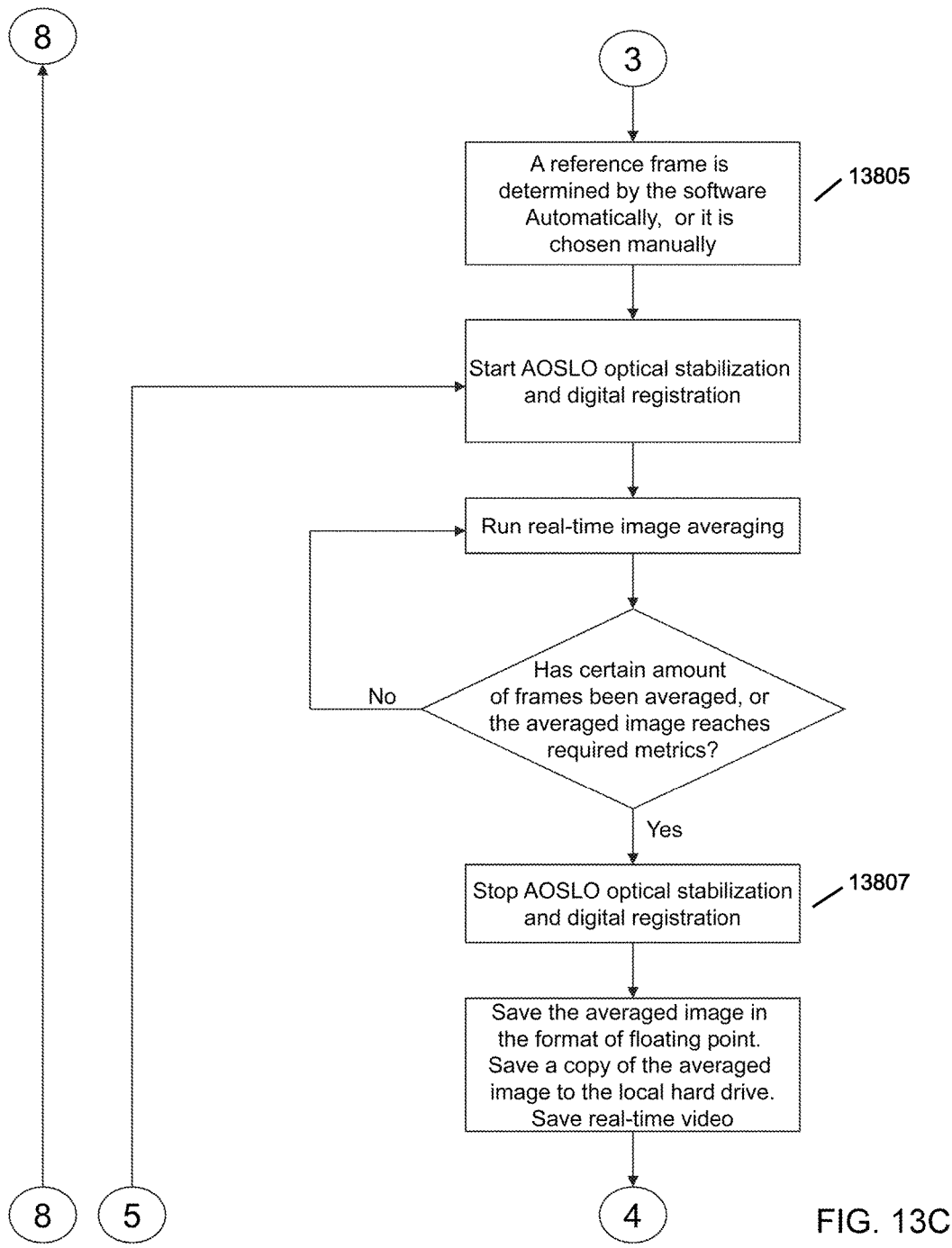
FIG. 13C shows a third page of the exemplary flow chart.
Figure 13D:
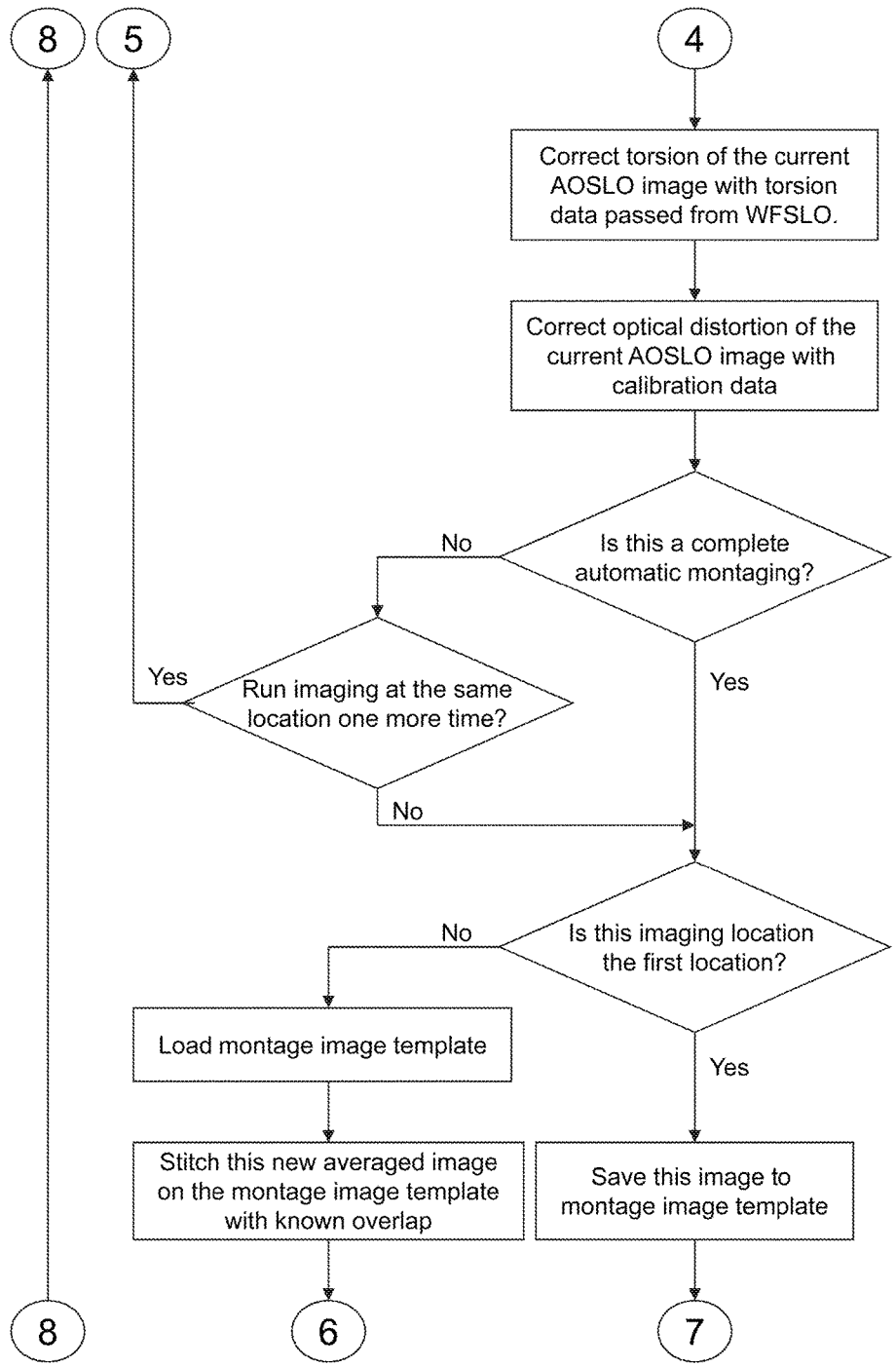
FIG. 13D shows a fourth page of the exemplary flow chart.
Figure 13E:
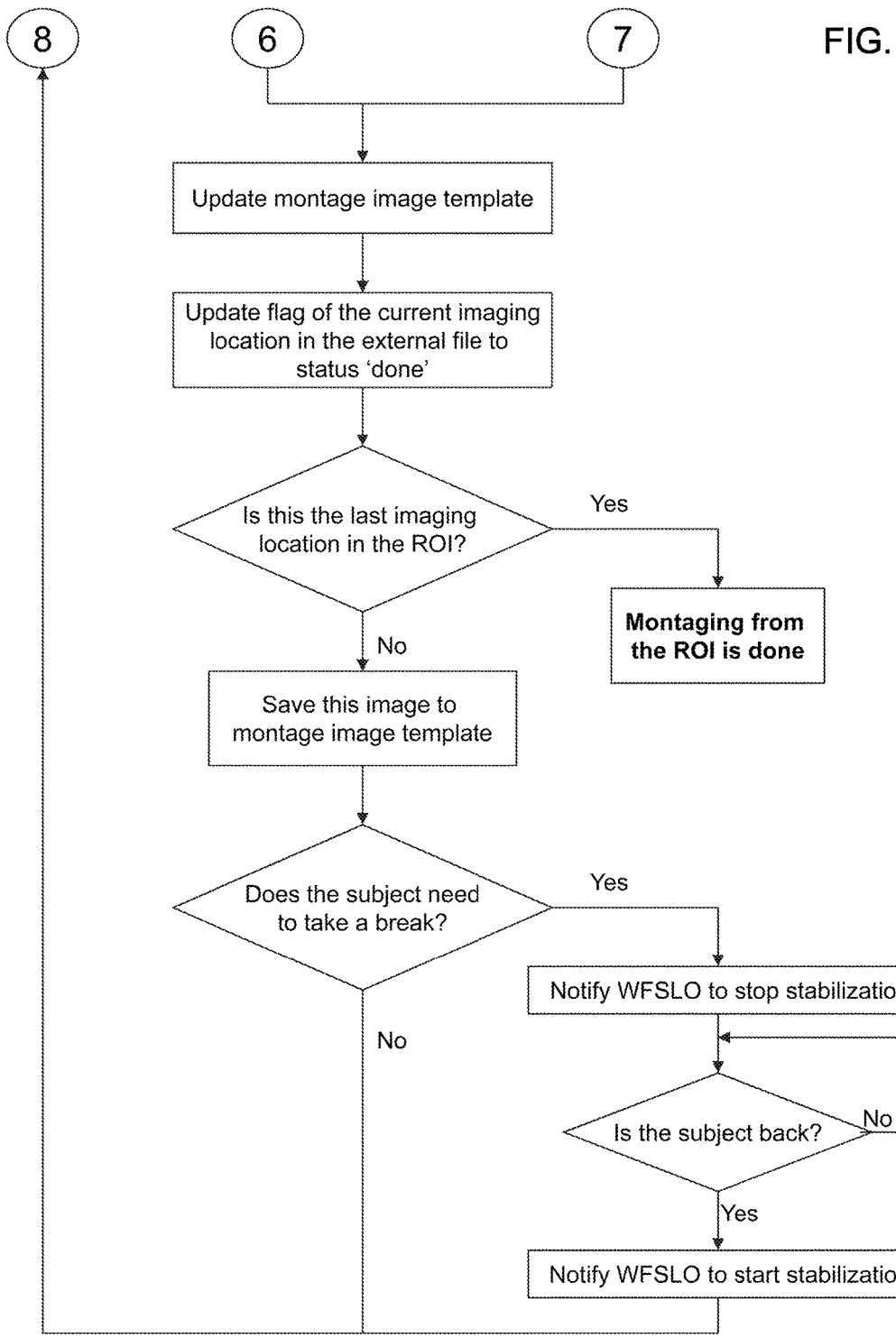
FIG. 13E shows a fifth page of the exemplary flow chart.

Step 13806 If this is the first average image, this image is saved in a large image template. If it is not, the image is stitched to the existing image template with known overlap area from step 13808 to step 13810. Before stitching this average image, optional rotation and/or stretch and/or compression can be performed to correct for eye torsion and/or optical distortion. The amount of image rotation due to eye torsion is calculated from equation (9) with the relationship, $$I_o(x, y) = \begin{bmatrix} \cos\Theta & -\sin\Theta \\ \sin\Theta & \cos\Theta \end{bmatrix} I_i(x, y) \quad (10)$$

where $I_i(x,y)$ is original image and $I_o(x,y)$ is rotated image. In this exemplary embodiment, optical distortion is corrected by use of a lookup table calibrated from the optical system. This lookup table recorded different optical distortion at different steering location of the retina. FIG. 12 shows how the shape of AOSLO imaging area is a function of steering location. For example, in FIG. 12, AOSLO imaging area (the raster image) is a square at the steering center, but its shape changes to something like a rotated-parallelogram or a diamond at steering location (+6°, +6°).

Step 13807 AOSLO software stops optical stabilization (deactivate M3) and digital registration.

Moving to the next narrow FOV location: Step 13808 The steering minor moves AOSLO imaging area to the next location with minimum amount of overlap. The starting point to determine the minimum amount of overlap is determined by two parameters: A) random eye motion after WFSLO and AOSLO optical stabilization which is ~1/10 of AOSLO image size with diseased eyes and ~1/20 of AOSLO image size with normal eyes, and B) nonlinear calibration of the steering range from step 13400. Therefore, for example, in diseased eyes, as long as steering is set to have about ¼ to ⅕ of the AOSLO image size, there should be enough overlap for successful image montaging.

Step 13809 The minimum amount of overlap in 13808 is also related directly to the step size of the steering minor.

Step 13810 Step size of the steering mirror is determined dynamically where live video from the new steering location is then correlated with the previous averaged image and adjusted to achieve the maximum step size.

Step 13811 Once the step size is determined, the AOSLO software repeats 13802-13805 to obtain a high SNR average image from the new imaging location, and stitch this image to the previously acquired images, at step 13806.

This process is repeated until the AOSLO montage covers the entire ROI. Overall, M3 is deactivated when the AOSLO steering mirror is moving, and M3 is reactivated when the steering mirror stops, because at each individual steering location the AOSLO reference image is different.

Semi-automatic mode: In an exemplary semi-automatic mode, the following procedure is executed.

The steering mirror moves the AOSLO image area automatically or manually to the first location, as illustrated in box "1" of FIG. 6.

Repeat step 13802.

An auto-focus thread (see step 13803, above) is activated or focus is adjusted manually to determine the best AOSLO image.

AO focus can be adjusted by updating the deformable mirror, or other optical and electronic components, such as by using the methods in the '195 application.

Repeat step 13805

The operator may choose to repeat the same imaging location for multiple times (e.g. at different foci) by executing steps 13902-13905.

Repeat step 13806.
Repeat step 13807.
Repeat step 13808.
Repeat step 13809.
Repeat step 13810.

Fine manual adjustment of steering step size is also provided on the user interface.

Repeat step 13811.

Again, M3 is deactivated when the AOSLO steering mirror is working, and M3 is reactivated when the steering mirror settles down, because in each individual steering location, the AOSLO reference image is different.

PART V—High Efficiency of the New Tracking/Montaging System

FIG. 14A shows an exemplary wide FOV image of the retina of a human eye for comparing the amount of AOSLO image motion with and without real-time eye tracking. With eye-tracking (FIG. 14A, AOSLO narrow FOV dashed rectangle), there is residual image motion of about 1/20-1/10 of AOSLO field size. In the exemplary stabilization system, the two fast tip/tilt minors which optically stabilize the AOSLO image are activated in real time to compensate eye motion. Without-tracking, the image motion can run 3-4 times of AOSLO field size (dotted rectangle) due to eye motion.

As described hereinabove, the high efficiency benefits from improvements in both the time domain and the spatial domain. In time domain, the new system and method uses significantly fewer frames (reducing imaging time, and exposure to LASER optical power) to achieve each high SNR averaged narrow FOV image (e.g. AOSLO image, FIG. 14B) at the imaging location (e.g. WFSLO, FIG. 14A, solid rectangle), because most of the individual images in this video sequence are inside the solid rectangle. For example, if averaging 100 frames is sufficient to construct a desired SNR threshold image, then recording slightly more than 100 frames will generally be sufficient with eye tracking. However to achieve the same SNR in the exemplary solid rectangle without eye tracking, significantly more frames (i.e. more imaging time) would be needed due to the relatively large motion of an un-stabilized system. Without eye tracking, many frames in the video sequence would have little overlap or substantially no overlap with the exemplary solid rectangle area.

Figure 15:
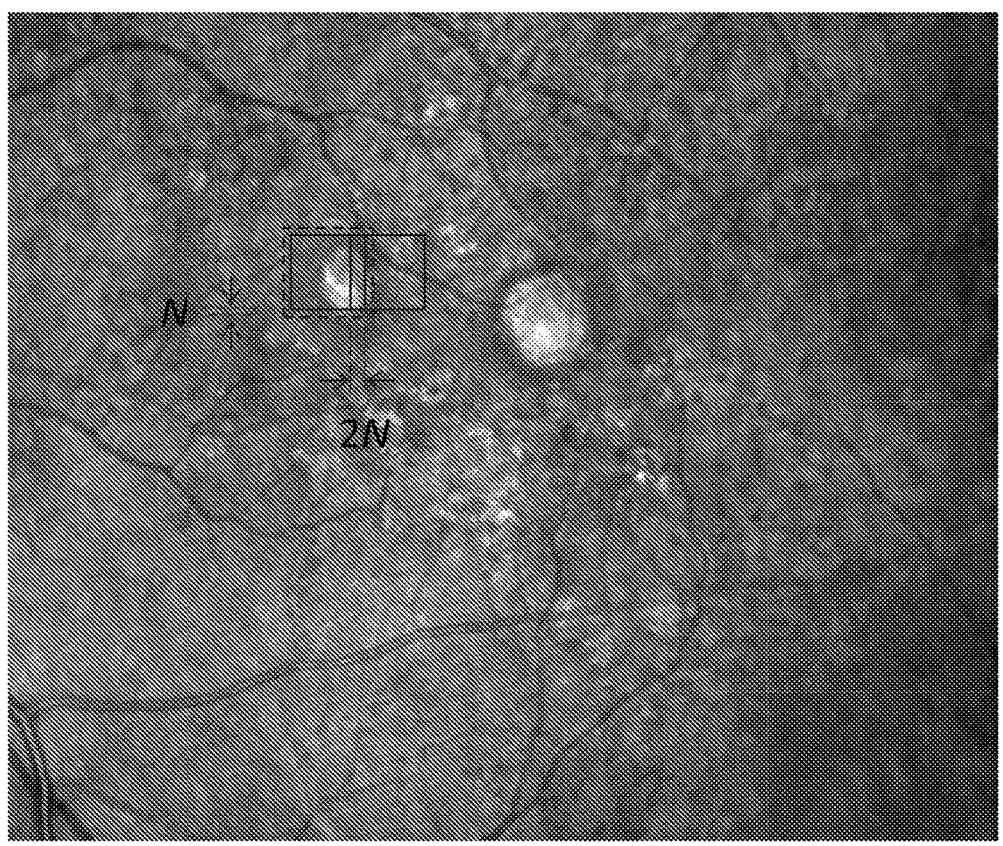
FIG. 15 shows a small overlapping of AOSLO narrow FOV images.
Figure 16:
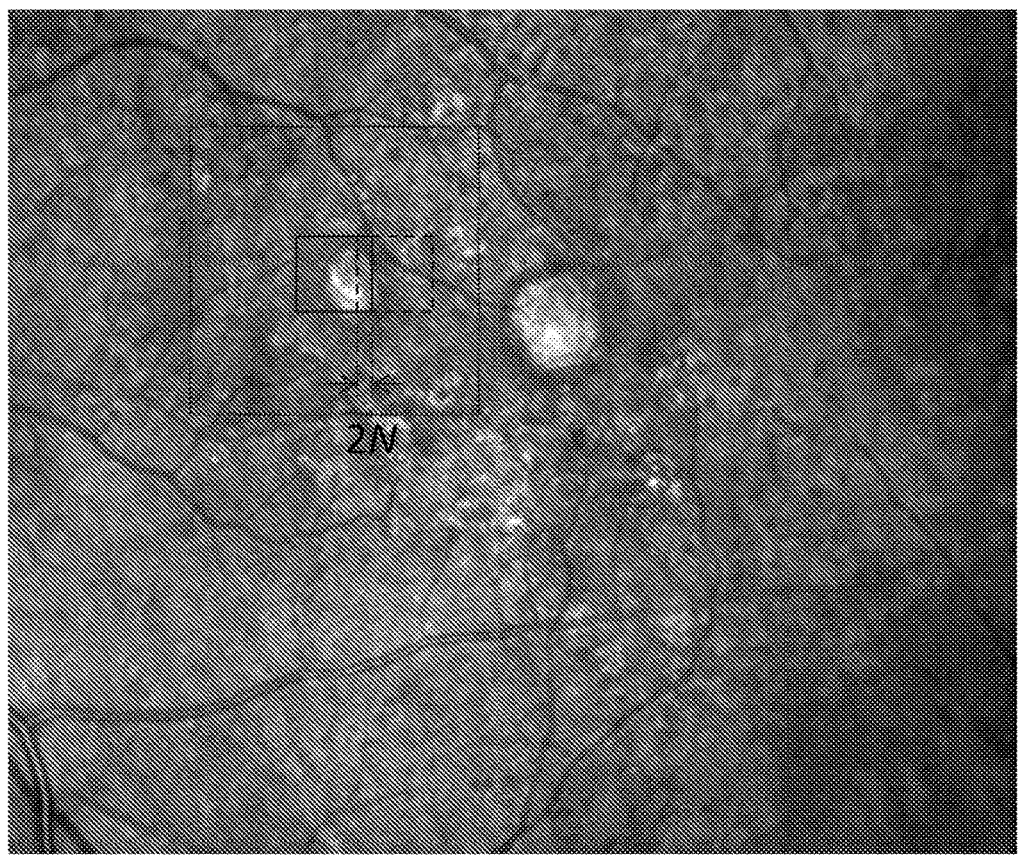
FIG. 16 shows a Wide FOV image illustrating the large overlap needed without image stabilization.
Figure 17:
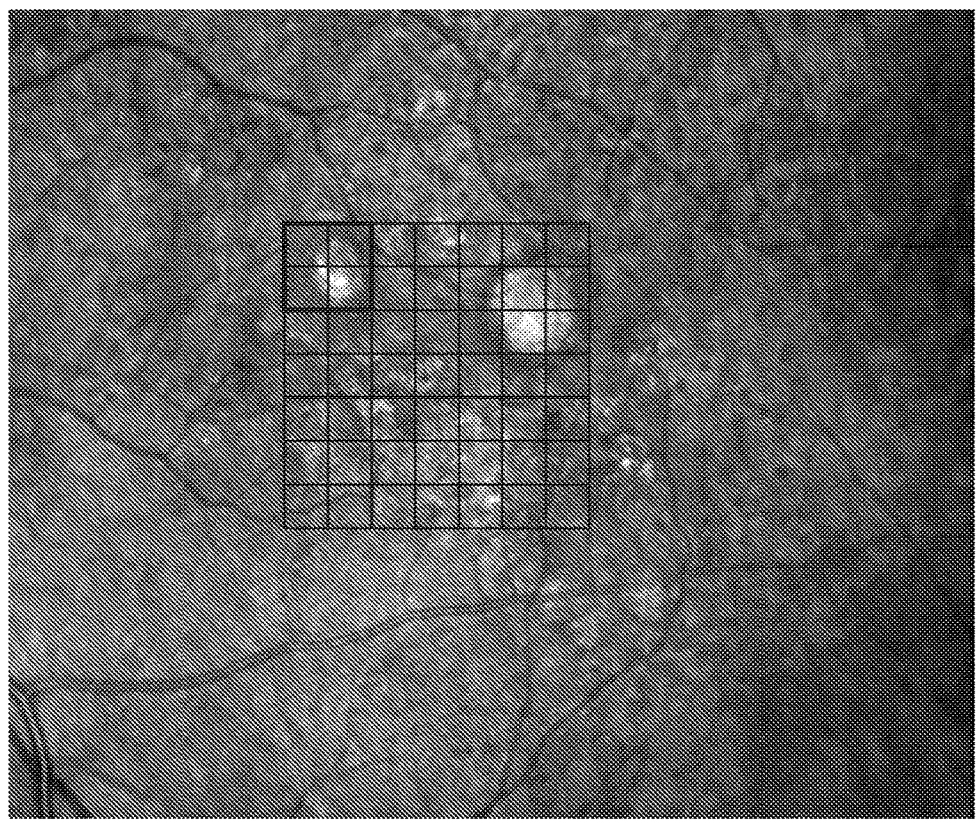
FIG. 17 shows an image illustrating the large number of narrow FOV images needed for montaging without image stabilization.
Figure 18:
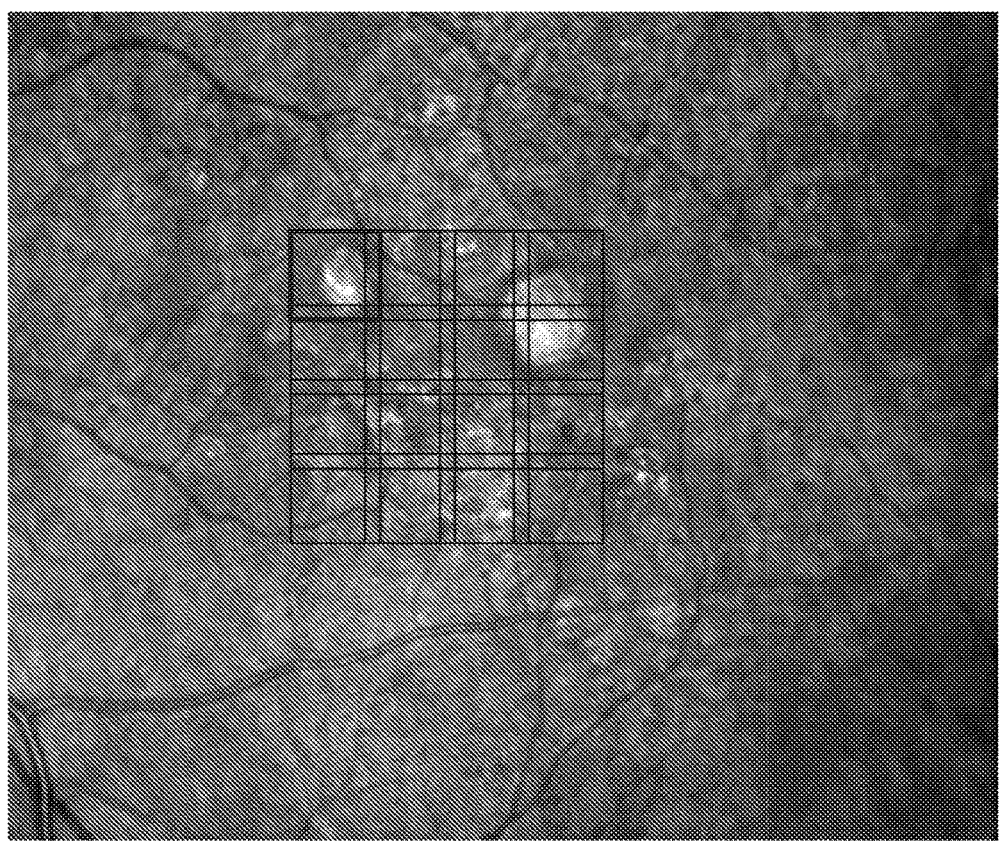
FIG. 18 shows a wide FOV image illustrating the relatively small number of AOSLO narrow FOV images used for montaging with an image stabilized SLO system.

The efficiency in the spatial domain is illustrated in FIG. 15 and FIG. 18 (with eye tracking) and FIG. 16 and FIG. 17 (without eye tracking). In FIG. 15, steering to the next location is nearly deterministic where the targeted overlapping amount in ~⅕-⅒ of AOSLO field size will guarantee the two imaging locations have sufficient amount of overlap for stitching (or montaging). Therefore, the tracking, steering, and montaging algorithm will work together to image the retina efficiently.

Thus, with real-time eye tracking, when AOSLO image can be steered to the next location, a targeted overlapping amount of 2N generally guarantees that two adjacent AOSLO locations will have a sufficient overlapped area, where N is the amount of AOSLO image motion. For example, the WFSLO image of FIG. 15, shows two overlapping AOSLO image footprints, where N is about ⅟₂₀ AOSLO field size in normal eyes and ⅒ field size in diseased eyes with poor fixation. N is typically a known value calculated from the eye-tracking algorithm. Therefore, the targeted overlapping amount 2N (~⅕ to ~⅒ of a frame size) becomes deterministic to steer the AOSLO imaging area to the next location.

However, as can be seen by the dotted area of the WFSLO image of FIG. 16, without eye tracking, steering AOSLO to the next location does not mean the AOSLO image will be physically locked to the next retinal location because of uncompensated large eye motion. To achieve a high SNR averaged image from the next imaging location will take significantly more imaging time (time domain) Because it is very difficult to control the overlapped area between these two imaging locations, it is technically difficult to stitch this average image to the one from the previous location. A traditional approach, which is very inefficient in the spatial domain, is to setup a large enough targeted overlapping area, e.g., a half AOSLO field size so that the two averaged images from the two imaging locations have sufficient overlap for stitching.

As can be seen in FIG. 16, without real-time eye tracking, steering the AOSLO imaging area to the next location with a certain amount of targeted overlapping, e.g., 2N, is very difficult, because the eye can randomly drift the AOSLO image to any retinal location inside the dotted rectangle. Without real-time eye tracking, the data acquisition software has to acquire a relatively large number of frames at the new steering location to achieve sufficient overlap against the averaged image from the previous imaging location. Also, steering has to be conservative enough to guarantee the two imaging locations have sufficient overlap for stitching the two final averaged images.

Without real-time eye tracking, when stitching should have more overlap area between adjacent imaging locations, sweeping through the same ROI should have more steering locations and more imaging time. Also without real-time eye tracking, as can be seen in FIG. 17, sweeping through the same ROI needs more steering locations because operation of the steering mirror has to be conservative enough to ensure sufficient overlapped area between the two adjacent imaging locations.

The new system and method described herein takes advantage of real-time tracking and therefore uses significantly less overlap between two adjacent imaging locations. Sweeping through the same ROI uses less steering locations and thus less imaging time. Because of small overlapped area between the two adjacent imaging locations, as can be seen on the exemplary WFSLO image of FIG. 18 with real-time eye tracking, sweeping through the same ROI uses less steering locations.

Figure 19:
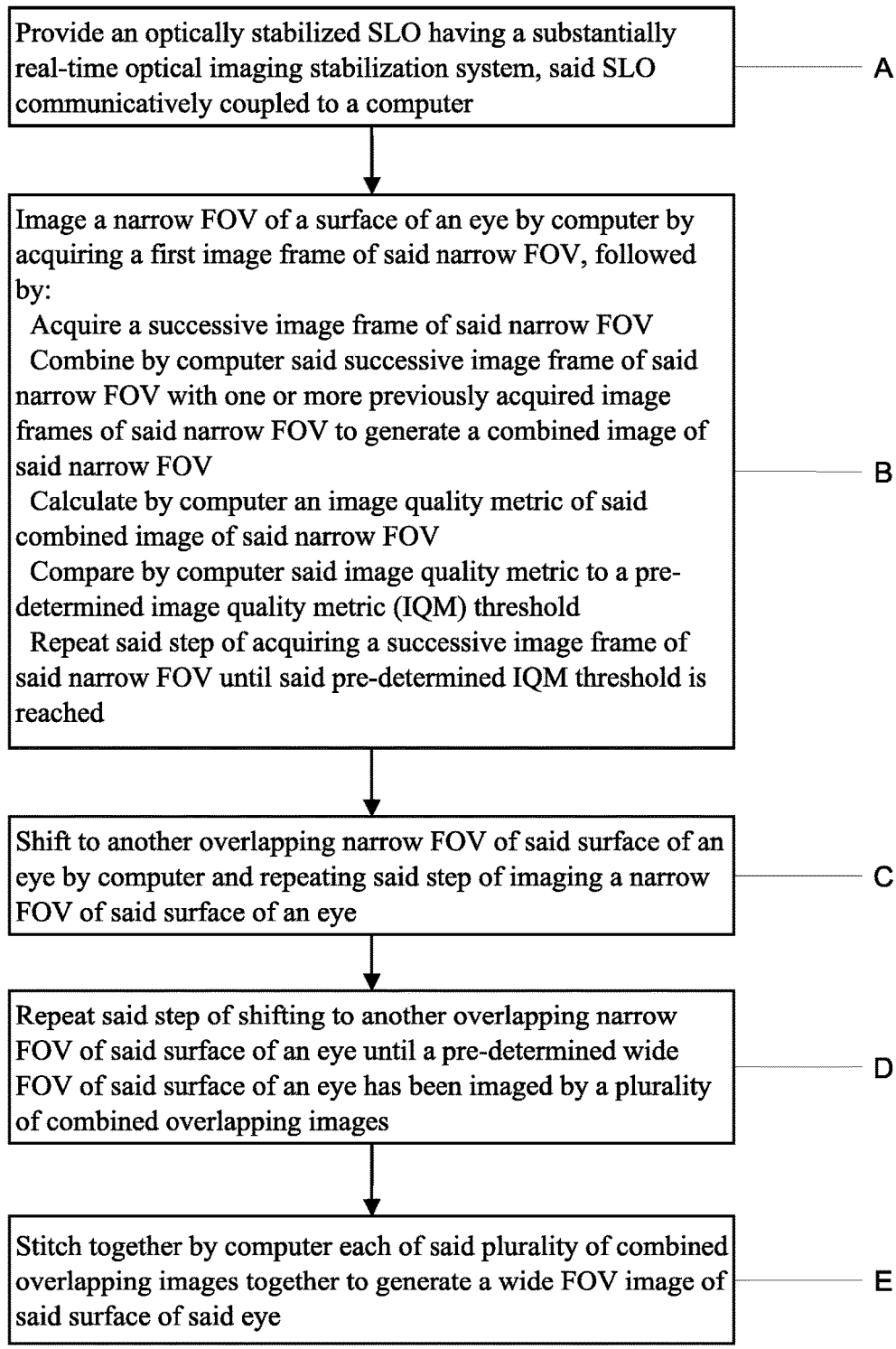
FIG. 19 shows a simplified flow chart of one exemplary method for real-time montaging.

FIG. 19 shows a simplified flow chart of one exemplary method for real-time montaging. A) Provide an optically stabilized SLO having a substantially real-time optical imaging stabilization system, said SLO communicatively coupled to a computer; B) Image a narrow FOV of a surface of an eye by computer by acquiring a first image frame of said narrow FOV, followed by: Acquire a successive image frame of said narrow FOV; Combine by computer said successive image frame of said narrow FOV with one or more previously acquired image frames of said narrow FOV to generate a combined image of said narrow FOV; Calculate by computer an image quality metric of said combined image of said narrow FOV; Compare by computer said image quality metric to a pre-determined image quality metric (IQM) threshold; Repeat said step of acquiring a successive image frame of said narrow FOV until said pre-determined IQM threshold is reached; C) Shift to another overlapping narrow FOV of said surface of an eye by computer and repeating said step of imaging a narrow FOV of said surface of an eye; D) Repeat said step of shifting to another overlapping narrow FOV of said surface of an eye until a pre-determined wide FOV of said surface of an eye has been imaged by a plurality of combined overlapping images; and E) Stitch together by computer each of said plurality of combined overlapping images together to generate a wide FOV image of said surface of said eye.

Figure 20:
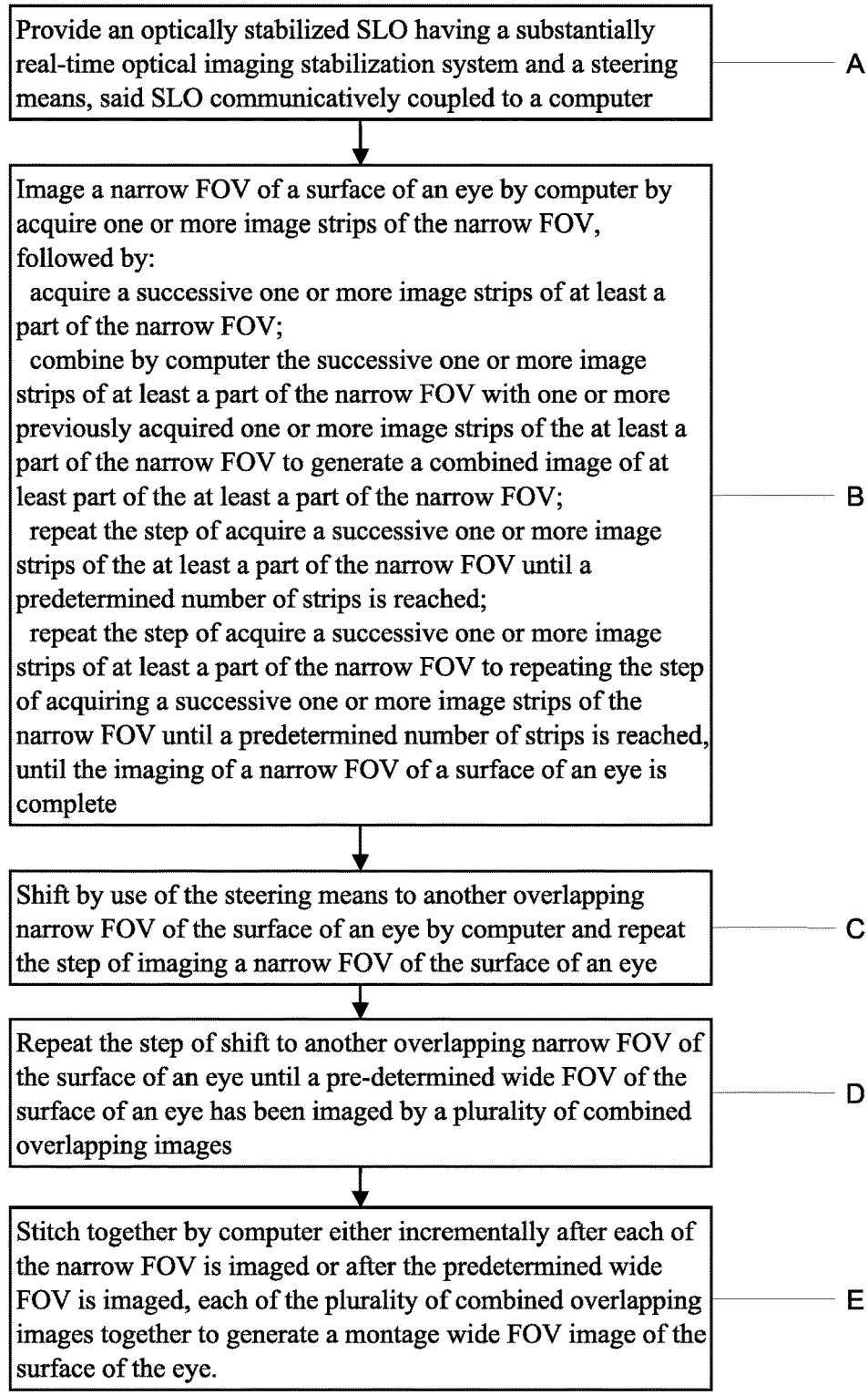
FIG. 20 shows a simplified flow chart of another exemplary method for real-time montaging based on a number of imaged strips or frames.

FIG. 20 shows a simplified flow chart of another exemplary method for real-time montaging where a predetermined number of successive strips are acquired and processed. A) Provide an optically stabilized SLO having a substantially real-time optical imaging stabilization system and a steering means, said SLO communicatively coupled to a computer; B) Image a narrow FOV of a surface of an eye by computer by acquire one or more image strips of the narrow FOV, followed by: acquire a successive one or more image strips of at least a part of the narrow FOV; combine by computer the successive one or more image strips of at least a part of the narrow FOV with one or more previously acquired one or more image strips of the at least a part of the narrow FOV to generate a combined image of at least part of the at least a part of the narrow FOV; repeat the step of acquire a successive one or more image strips of the at least a part of the narrow FOV until a predetermined number of strips is reached; repeat the step of acquire a successive one or more image strips of at least a part of the narrow FOV to repeating the step of acquiring a successive one or more image strips of the narrow FOV until a predetermined number of strips is reached, until the imaging of a narrow FOV of a surface of an eye is complete; C) Shift by use of the steering means to another overlapping narrow FOV of the surface of an eye by computer and repeat the step of imaging a narrow FOV of the surface of an eye; D) Repeat the step of shift to another overlapping narrow FOV of the surface of an eye until a pre-determined wide FOV of the surface of an eye has been imaged by a plurality of combined overlapping images; and E) Stitch together by computer either incrementally after each of the narrow FOV is imaged or after the predetermined wide FOV is imaged, each of the plurality of combined overlapping images together to generate a montage wide FOV image of the surface of the eye.

Figure 21:
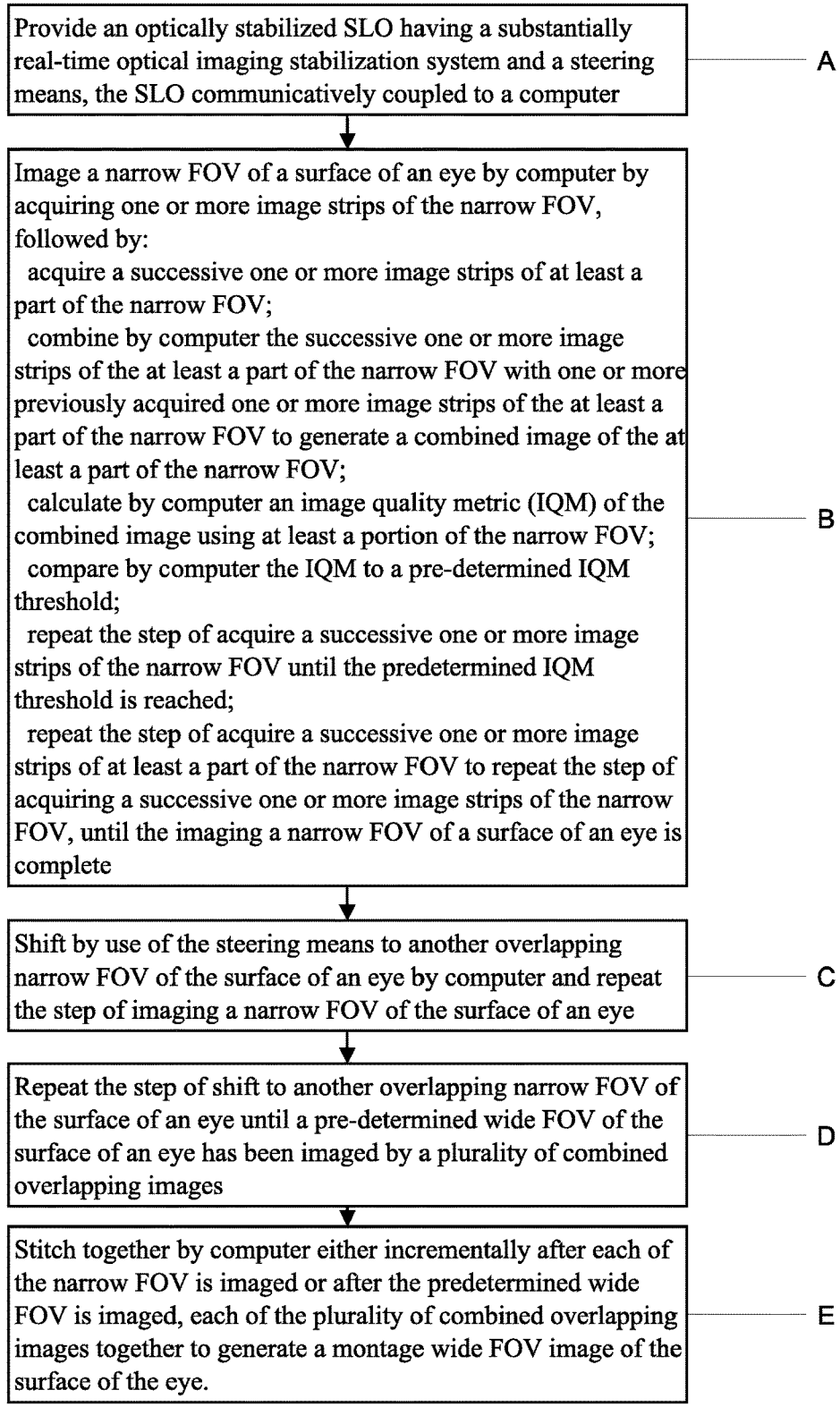
FIG. 21 shows a simplified flow chart of yet another exemplary method for real-time montaging that makes use of an image quality metric (IQM).

FIG. 21 shows a simplified flow chart of one exemplary method for real-time montaging where successive strips are acquired and processed and successive strips are acquired until a predetermined IQM of at least a portion of an image is reached. A) Provide an optically stabilized SLO having a substantially real-time optical imaging stabilization system and a steering means, the SLO communicatively coupled to a computer; B) Image a narrow FOV of a surface of an eye by computer by acquiring one or more image strips of the narrow FOV, followed by: acquire a successive one or more image strips of at least a part of the narrow FOV; combine by computer the successive one or more image strips of the at least a part of the narrow FOV with one or more previously acquired one or more image strips of the at least a part of the narrow FOV to generate a combined image of the at least a part of the narrow FOV; calculate by computer an image quality metric (IQM) of the combined image using at least a portion of the narrow FOV; compare by computer the IQM to a pre-determined IQM threshold; repeat the step of acquire a successive one or more image strips of the narrow FOV until the predetermined IQM threshold is reached; repeat the step of acquire a successive one or more image strips of at least a part of the narrow FOV to repeat the step of acquiring a successive one or more image strips of the narrow FOV, until the imaging a narrow FOV of a surface of an eye is complete; C) Shift by use of the steering means to another overlapping narrow FOV of the surface of an eye by computer and repeat the step of imaging a narrow FOV of the surface of an eye; D) Repeat the step of shift to another overlapping narrow FOV of the surface of an eye until a pre-determined wide FOV of the surface of an eye has been imaged by a plurality of combined overlapping images; and E) Stitch together by computer either incrementally after each of the narrow FOV is imaged or after the predetermined wide FOV is imaged, each of the plurality of combined overlapping images together to generate a montage wide FOV image of the surface of the eye.

Computer software and or firmware to run a SLO montaging system as described hereinabove is typically supplied and/or stored on a computer readable non-transitory storage medium. A computer readable non-transitory storage medium as non-transitory data storage includes any data stored on any suitable media in a non-fleeting manner. Such data storage includes any suitable computer readable non-transitory storage medium, including, but not limited to hard drives, non-volatile RAM, SSD devices, CDs, DVDs, etc.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

REFERENCES

1. Stevenson, et. al. in "Correcting for miniature eye movements in high resolution scanning laser ophthalmoscopy" in Ophthalmic Technologies XV, Proceedings of The International Society for Optics and Photonics (SPIE), Vol. 5688A, 2005.
2. G. Huang, Z. Zhong, W. Zou, and S. A. Burns, ""Lucky Averaging": Quality improvement on Adaptive Optics Scanning Laser Ophthalmoscope Images," Opt Lett 36, 3786-3788 (2011).
3. X. Cheng, A. Bradley, and L. N. Thibos, "Predicting subjective judgment of best focus with objective image quality metrics," J Vis 4, 7 (2004).
4. J. A. Saghri, P. S. Cheatham, and A. Habibi, "Image Quality Measure Based On A Human Visual System Model," Opt. Eng 28, 287813-287813-(1989).
5. N. B. Nill and B. Bouzas, "Objective image quality measure derived from digital image power spectra," Opt. Eng 31, 813-825 (1992).
6. Z. Wang, E. P. Simoncelli, and H. Hughes, "Local phase coherence and the perception of blur," in In Adv. Neural Information Processing Systems, 2004 (n.d.), pp. 786-792.
7. L. Firestone, K. Cook, K. Culp, N. Talsania, and K. Preston Jr, "Comparison of autofocus methods for automated microscopy," Cytometry 12, 195-206 (1991).
8. D. Shaked and I. Tastl, "Sharpness measure: towards automatic image enhancement," in IEEE International Conference on Image Processing, 2005. ICIP 2005 (2005), Vol. 1, pp. I-937-40.
9. R. Ferzli and L. J. Karam, "No-reference objective wavelet based noise immune image sharpness metric," in IEEE International Conference on Image Processing, 2005. ICIP 2005 (2005), Vol. 1, pp. I-405-8.
10. S. J. Erasmus and K. C. A. Smith, "An automatic focusing and astigmatism correction system for the SEM and CTEM," Journal of Microscopy 127, 185-199 (1982).
11. C. Batten, "Autofocusing and Astigmatism Correction in the Scanning Electron Microscope," University of Cambridge (2000).
12. J. Caviedes and F. Oberti, "A new sharpness metric based on local kurtosis, edge and energy information," Signal Processing: Image Communication 19, 147-161 (2004).
13. N. Ng Kuang Chern, P. A. Neow, and V. M. H. Ang, "Practical issues in pixel-based autofocusing for machine vision," in IEEE International Conference on Robotics and Automation, 2001. Proceedings 2001 ICRA (2001), Vol. 3, pp. 2791-2796 vol. 3.
14. P. Marziliano, F. Dufaux, S. Winkler, and T. Ebrahimi, "A no-reference perceptual blur metric," in 2002 International Conference on Image Processing. 2002. Proceedings (2002), Vol. 3, pp. III-57-III-60 vol. 3.
15. X. Li, "Blind image quality assessment," in 2002 International Conference on Image Processing. 2002. Proceedings (2002), Vol. 1, pp. I-449-I-452 vol. 1.
16. S. Gabarda and G. Cristóbal, "Blind image quality assessment through anisotropy," J Opt Soc Am A Opt Image Sci Vis 24, B42-51 (2007).
17. E. Cohen and Y. Yitzhaky, "No-reference assessment of blur and noise impacts on image quality," SIViP 4, 289-302 (2010).

What is claimed is:

1. A method to montage a plurality of scanning LASER ophthalmoscope (SLO) narrow field of view (FOV) images comprising the steps of:

providing an optically stabilized SLO having a substantially real-time optical imaging stabilization system and a steering means, said SLO communicatively coupled to a computer;

imaging a narrow FOV of a surface of an eye by computer by acquiring one or more image strips of said narrow FOV, followed by:

acquiring a successive one or more image strips of at least a part of said narrow FOV;

combining by computer said successive one or more image strips of at least a part of said narrow FOV with one or more previously acquired one or more image strips of said at least a part of said narrow FOV to generate a combined image of at least part of said at least a part of said narrow FOV;

repeating said step of acquiring a successive one or more image strips of said at least a part of said narrow FOV until a predetermined number of strips is reached;

repeating said step of acquiring a successive one or more image strips of at least a part of said narrow FOV to repeating said step of acquiring a successive one or more image strips of said narrow FOV until a predetermined number of strips is reached, until said imaging a narrow FOV of a surface of an eye is complete; and shifting by use of said steering means to another overlapping narrow FOV of said surface of an eye by computer and repeating said step of imaging a narrow FOV of said surface of an eye;

repeating said step of shifting to another overlapping narrow FOV of said surface of an eye until a predetermined wide FOV of said surface of an eye has been imaged by a plurality of combined overlapping images; and stitching together by computer either incrementally after each of said narrow FOV is imaged or after said predetermined wide FOV is imaged, each of said plurality of combined overlapping images together to generate a montage wide FOV image of said surface of said eye.

2. The method of claim 1, wherein said one or more image strips comprise an entire frame.

3. A method to montage a plurality of scanning LASER ophthalmoscope (SLO) narrow field of view (FOV) images comprising the steps of:

providing an optically stabilized SLO having a substantially real-time optical imaging stabilization system and a steering means, said SLO communicatively coupled to a computer;

imaging a narrow FOV of a surface of an eye by computer by acquiring one or more image strips of said narrow FOV, followed by:

acquiring a successive one or more image strips of at least a part of said narrow FOV;

combining by computer said successive one or more image strips of said at least a part of said narrow FOV with one or more previously acquired one or more image strips of said at least a part of said narrow FOV to generate a combined image of said at least a part of said narrow FOV;

calculating by computer an image quality metric (IQM) of said combined image using at least a portion of said narrow FOV;

comparing by computer said IQM to a pre-determined IQM threshold;

repeating said step of acquiring a successive one or more image strips of said narrow FOV until said predetermined IQM threshold is reached;

repeating said step of acquiring a successive one or more image strips of at least a part of said narrow FOV to repeating said step of acquiring a successive one or more image strips of said narrow FOV, until said imaging a narrow FOV of a surface of an eye is complete; and shifting by use of said steering means to another overlapping narrow FOV of said surface of an eye by computer and repeating said step of imaging a narrow FOV of said surface of an eye;

repeating said step of shifting to another overlapping narrow FOV of said surface of an eye until a predetermined wide FOV of said surface of an eye has been imaged by a plurality of combined overlapping images; and stitching together by computer either incrementally after each of said narrow FOV is imaged or after said predetermined wide FOV is imaged, each of said plurality of combined overlapping images together to generate a montage wide FOV image of said surface of said eye.

4. The method of claim 3, wherein said one or more image strips comprises an entire frame.

5. The method of claim 3, wherein said step of providing an optically stabilized SLO comprises the step of providing an adaptive optics scanning light ophthalmoscope (AOSLO) having a substantially real-time optical imaging stabilization system.

6. The method of claim 3, wherein said step of shifting by said steering means to another overlapping narrow FOV of said surface of an eye comprises shifting to another overlapping narrow FOV of said surface of an eye with about a 20% or less overlap.

7. The method of claim 3, wherein said step of comparing by computer said IQM comprises comparing by computer said IQM based on a power measurement.

8. The method of claim 3, wherein said step of comparing by computer said IQM comprises comparing by computer said IQM based on a spatial frequency content measurement.

9. The method of claim 3, wherein said step of comparing by computer said IQM comprises comparing by computer an IQM based on a contrast or sharpness measurement.

10. The method of claim 3, wherein said step of comparing by computer said IQM comprises comparing by computer said IQM by use of a texture based measurement.

11. The method of claim 3, wherein said step of comparing by computer said IQM comprises comparing by computer said IQM based on a probability density function measurement.

12. The method of claim 3, further including before said step of repeating said step of shifting to another overlapping narrow FOV of said surface of an eye until a predetermined wide FOV of said surface of an eye has been imaged, the step of selecting said pre-determined wide FOV by use of a Fundus wide field camera communicatively coupled to said computer.

* * * * *